United States Patent
Wasson et al.

(10) Patent No.: US 10,292,630 B2
(45) Date of Patent: *May 21, 2019

(54) OPTICAL SENSOR FOR BANDAGE TYPE MONITORING DEVICE

(71) Applicant: Verily Life Sciences LLC, Mountain View, CA (US)

(72) Inventors: Jaclyn Leverett Wasson, Berkeley, CA (US); William James Biederman, Fox Island, WA (US); Zenghe Liu, Alameda, CA (US); Brian Otis, Saratoga, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 380 days.

This patent is subject to a terminal disclaimer.

(21) Appl. No.: 14/727,368

(22) Filed: Jun. 1, 2015

(65) Prior Publication Data

US 2016/0345872 A1    Dec. 1, 2016

(51) Int. Cl.
*A61B 5/00* (2006.01)
*A61B 5/1459* (2006.01)
(Continued)

(52) U.S. Cl.
CPC .......... *A61B 5/1459* (2013.01); *A61B 5/0004* (2013.01); *A61B 5/1451* (2013.01);
(Continued)

(58) Field of Classification Search
CPC ............ A61B 5/1459; A61B 5/150022; A61B 5/14532; A61B 5/1455; A61B 5/688;
(Continued)

(56) References Cited

U.S. PATENT DOCUMENTS

| 4,677,528 A | 6/1987 | Miniet |
| 5,605,152 A | 2/1997 | Slate et al. |

(Continued)

FOREIGN PATENT DOCUMENTS

| JP | H03-024452 A | 2/1991 |
| JP | 2007-205989 A | 8/2007 |

(Continued)

OTHER PUBLICATIONS

Partial International Search Report of International Application No. PCT/US2016/023511 dated Jun. 13, 2016.
(Continued)

*Primary Examiner* — Navin Natnithithadha
*Assistant Examiner* — Andrey Shostak
(74) *Attorney, Agent, or Firm* — McDonnell Boehnen Hulbert & Berghoff LLP

(57) ABSTRACT

A flexible, body-mountable analyte sensing device includes a flexible substrate configured for mounting to skin of a living body. The sensing device additionally includes optical fiber attached to the flexible substrate and configured to penetrate the skin such that an analyte-sensitive substance disposed on the end of the optical fiber can detect an analyte in interstitial fluid. A color, fluorescence intensity, or other optical property of the analyte-sensitive substance is related to the concentration or other property of the analyte. Light reflected, scattered, fluorescently emitted, or otherwise emitted from the analyte-sensitive substance is transmitted via the optical fiber and detected by a light sensor on the flexible substrate. Such emitted light can be emitted in response to illumination of the analyte-sensitive substance via the optical fiber. The sensing device is configured to wirelessly indicate detected concentrations or other information about the analyte in the interstitial fluid.

19 Claims, 7 Drawing Sheets

(51) Int. Cl.
*A61B 5/145* (2006.01)
*A61B 5/1455* (2006.01)
*A61B 5/15* (2006.01)
*A61B 5/1473* (2006.01)

(52) U.S. Cl.
CPC ........ *A61B 5/1455* (2013.01); *A61B 5/14532* (2013.01); *A61B 5/150022* (2013.01); *A61B 5/688* (2013.01); *A61B 5/6847* (2013.01); *A61B 5/0071* (2013.01); *A61B 5/0084* (2013.01); *A61B 5/14735* (2013.01); *A61B 5/6801* (2013.01); *A61B 5/685* (2013.01); *A61B 2562/12* (2013.01)

(58) Field of Classification Search
CPC ... A61B 5/1451; A61B 5/0004; A61B 5/6847; A61B 5/14735; A61B 5/685; A61B 5/0084; A61B 5/0071; A61B 5/6801; A61B 2562/12
See application file for complete search history.

(56) References Cited

U.S. PATENT DOCUMENTS

| | | | |
|---|---|---|---|
| 5,957,854 | A | 9/1999 | Besson et al. |
| 7,652,188 | B2 | 1/2010 | Levanon et al. |
| 7,949,382 | B2 | 5/2011 | Jina |
| 8,202,697 | B2 | 6/2012 | Holmes |
| 8,326,652 | B2 | 12/2012 | Sweeney |
| 8,385,998 | B2 | 2/2013 | Zhang et al. |
| 8,512,245 | B2 | 8/2013 | Markle et al. |
| 8,609,426 | B2 | 12/2013 | Silver |
| 8,764,657 | B2 | 7/2014 | Curry et al. |
| 8,792,954 | B2 | 7/2014 | Vojcic et al. |
| 8,849,379 | B2 | 9/2014 | Abreu |
| 8,956,289 | B2 | 2/2015 | Kitajima et al. |
| 8,972,196 | B2 | 3/2015 | Peyser et al. |
| 8,979,755 | B2 * | 3/2015 | Szydlo-Moore ..... A61B 5/0002 600/301 |
| 9,007,781 | B2 | 4/2015 | Moein et al. |
| 9,072,476 | B2 | 7/2015 | Shah et al. |
| 9,248,232 | B2 | 2/2016 | Yodfat et al. |
| 2003/0208113 | A1 | 11/2003 | Mault et al. |
| 2005/0113658 | A1 * | 5/2005 | Jacobson ........... A61B 5/14532 600/342 |
| 2005/0148887 | A1 | 7/2005 | Reiter et al. |
| 2007/0073129 | A1 * | 3/2007 | Shah ................. A61B 5/14532 600/365 |
| 2007/0100219 | A1 * | 5/2007 | Sweitzer ............. A61B 5/0002 600/323 |
| 2007/0100222 | A1 | 5/2007 | Mastrototaro et al. |
| 2008/0009692 | A1 | 1/2008 | Stafford |
| 2008/0079565 | A1 | 4/2008 | Koyama |
| 2008/0114227 | A1 | 5/2008 | Haar et al. |
| 2010/0094112 | A1 | 4/2010 | Heller et al. |
| 2010/0198034 | A1 | 8/2010 | Thomas et al. |
| 2010/0200538 | A1 | 8/2010 | Petisce et al. |
| 2010/0268046 | A1 | 10/2010 | Say et al. |
| 2010/0270180 | A1 | 10/2010 | Liu et al. |
| 2011/0077490 | A1 * | 3/2011 | Simpson ............ A61B 5/14532 600/345 |
| 2011/0319734 | A1 | 12/2011 | Gottlieb et al. |
| 2012/0018302 | A1 | 1/2012 | Shiraki et al. |
| 2012/0190989 | A1 | 7/2012 | Kaiser et al. |
| 2012/0277667 | A1 * | 11/2012 | Yodat ................... A61B 5/1451 604/65 |
| 2012/0296187 | A1 | 11/2012 | Henning et al. |
| 2013/0041235 | A1 | 2/2013 | Rogers et al. |
| 2013/0060105 | A1 * | 3/2013 | Shah .................... A61B 5/6849 600/316 |
| 2013/0076531 | A1 * | 3/2013 | San Vicente ......... A61B 5/0015 340/870.02 |
| 2013/0131478 | A1 | 5/2013 | Simpson et al. |
| 2013/0197332 | A1 | 8/2013 | Luoisano et al. |
| 2013/0274563 | A1 | 10/2013 | Duesterhoft et al. |
| 2014/0180137 | A1 | 6/2014 | Stivoric et al. |
| 2014/0275899 | A1 * | 9/2014 | Gottlieb ............. A61B 5/14532 600/347 |
| 2015/0005589 | A1 | 1/2015 | Bly et al. |
| 2015/0018639 | A1 | 1/2015 | Stafford |
| 2015/0119662 | A1 * | 4/2015 | Larson ............... A61B 5/14532 600/316 |

FOREIGN PATENT DOCUMENTS

| | | | | |
|---|---|---|---|---|
| JP | 2008-109847 | A | 5/2008 | |
| JP | 2009-508639 | T | 3/2009 | |
| JP | 2012-026910 | A | 2/2012 | |
| JP | 2012-517597 | T | 8/2012 | |
| JP | 2012-531948 | T | 12/2012 | |
| JP | 2013-009710 | A | 1/2013 | |
| JP | 2013-534439 | T | 9/2013 | |
| JP | 2014-523793 | T | 9/2014 | |
| JP | 2014-529481 | T | 11/2014 | |
| WO | 2005094285 | A2 | 10/2005 | |
| WO | 2013028784 | A1 | 2/2013 | |
| WO | WO 2013028784 | A1 * | 2/2013 | ........... G01N 21/645 |
| WO | 2013172929 | A1 | 11/2013 | |
| WO | 2014145484 | A2 | 9/2014 | |
| WO | 2014159229 | A1 | 10/2014 | |
| WO | 2015017712 | | 2/2015 | |
| WO | 2015017712 | A1 | 2/2015 | |
| WO | 2015061593 | A1 | 4/2015 | |

OTHER PUBLICATIONS

International Search Report and Written Opinion of International Application No. PCT/US2016/023511 dated Jun. 3, 016 (dated Aug. 4, 2016).
Getting starting with Guardian REAL-Time Continuous Glucose Monitoring, product guide, 2009, Medtronic, Northridge, CA.
Dexcom G4 Platinum Professional Continuous Glucose Monitoring System, User's guide, 2014, Dexcom, IncG.
Jonah Comstock, "Medtronic showcases smartphone-enabled continuous glucose monitoring," MobiHealthNews, http://mobihealthnews.com, Sep. 24, 2014.
International Search Report and Written Opinion of International Application No. PCT/US2016/017946 dated Jun. 1, 2016.
Getting starting with Guardian REAL-Time Continuous Glucose Monitoring, Product manual, 2009, Medtronic, Northridge, CA.
Guardian REAL-Time Continuous Glucose Monitoring System, User guide, 2006, Medtronic MiniMed, Northridge, CA.
Dexcom G4 Platinum Professional Continuous Glucose Monitoring System, User's guide, 2014, Dexcom, Inc.
Dexcom G4 Platinum Continuous Glucose Monitoring System, Quick start guide, 2013, Dexcom, Inc. San Diego, CA.
Jonah Comstock, "Medtronic showcases smartphone-enabled continuous glucose monitoring," MobiHealthNews, http://mobihealthnew.com, Sep. 24, 2014.
Pickup, J.C., et al., "Fluorescence-based glucose sensors," Biosensors and Bioelectronics, p. 2555-2565, 20 (2005).
Klonoff, D.C., "Overview of Fluorescence Glucose Sensing: A Technology with a Bright Future," Journal of Diabetes Science and Technology, p. 1242-1250, vol. 6, Issue 6, (2012).
International Search Report and Written Opinion for International Application No. PCT/US2016/017512 dated May 6, 2016.

* cited by examiner

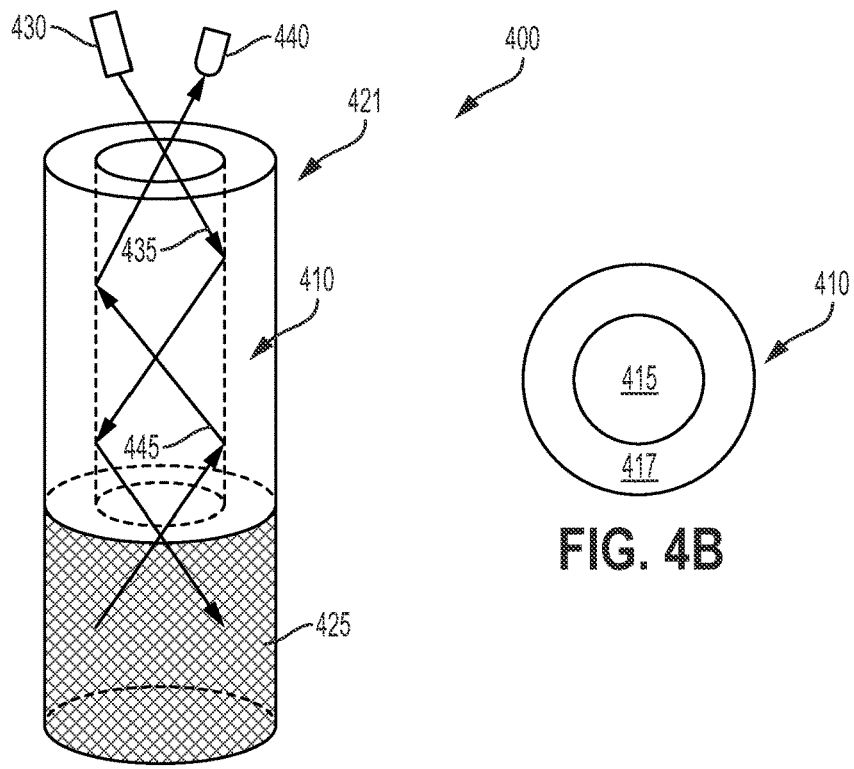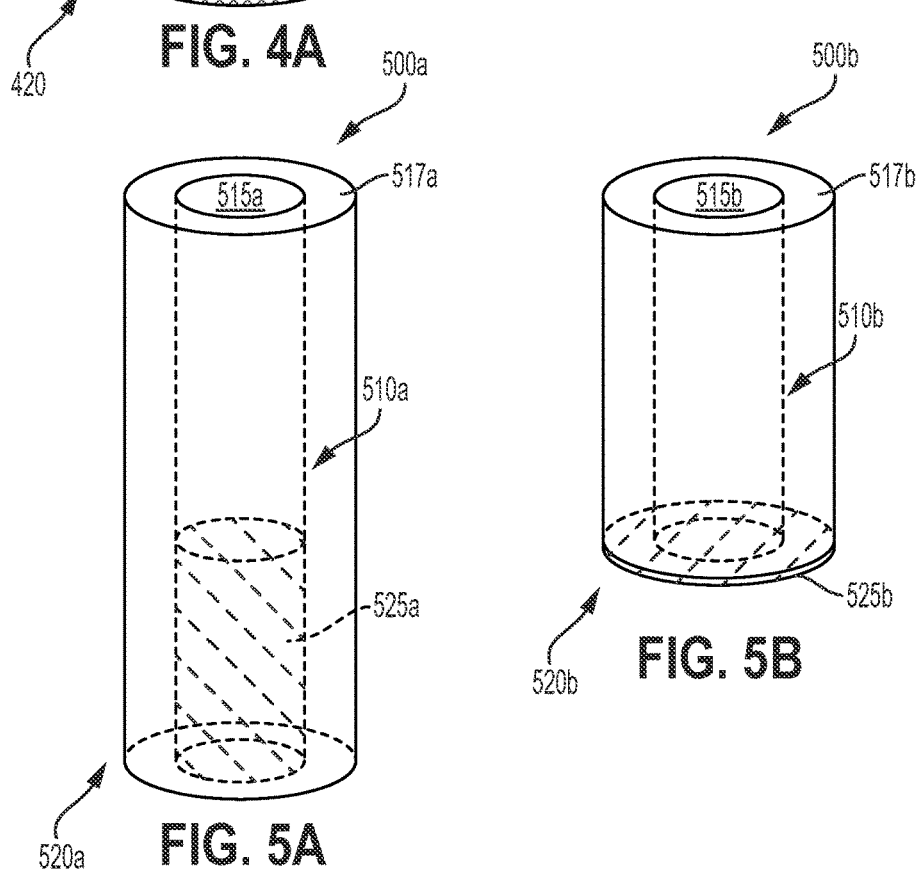

OPTICAL SENSOR FOR BANDAGE TYPE MONITORING DEVICE

BACKGROUND

Unless otherwise indicated herein, the materials described in this section are not prior art to the claims in this application and are not admitted to be prior art by inclusion in this section.

Certain medical conditions or states can be characterized by slow changes of a physiological property (e.g., a blood glucose concentration) over long periods of time and/or by infrequent, short-timescale events. Such physiological properties can be measured periodically (e.g., by periodically accessing blood of a person). Additionally or alternatively, an implanted or wearable device could be employed to provide continuous or near-continuous measurement of such physiological properties. Such implantable or wearable devices can be battery powered and/or powered by radio frequency energy or other wireless energy sources. Further, such devices can be configured to indicate measured physiological properties wirelessly (e.g., by using an RFID antenna and transmitter, by using a BLUETOOTH antenna and transmitter).

SUMMARY

Some embodiments of the present disclosure provide a body-mountable device including: (i) a flexible substrate that is configured to be mounted to a skin surface; (ii) a sensor probe that is attached by a first end of the sensor probe to the flexible substrate and that has second end that is configured to extend beneath the skin surface to contact interstitial fluid, wherein the sensor probe includes an optical fiber extending from the first end of the sensor probe to the second end of the sensor probe; (iii) an analyte-sensitive substance that is disposed at the second end of the sensor probe and that has an optical property affected by an analyte in the interstitial fluid; (iv) a light detector; and (v) one or more electronic components disposed on the flexible substrate that are configured to (a) operate the light detector to detect, via the optical fiber, a property of light emitted from the analyte-sensitive substance and (b) indicate data related to the detected property of the emitted light.

Some embodiments of the present disclosure provide a body-mountable device including: (i) a flexible substrate that is configured to be mounted to a skin surface; (ii) probe means that are attached by a first end of the probe means to the flexible substrate and that have second end that is configured to extend beneath the skin surface to contact interstitial fluid, wherein the probe means include an optical fiber extending from the first end of the probe means to the second end of the probe means; (iii) an analyte-sensitive substance that is disposed at the second end of the probe means and that has an optical property affected by an analyte in the interstitial fluid; (iv) light detecting means; and (v) one or more electronic components disposed on the flexible substrate that are configured to (a) operate the light detecting means to detect, via the optical fiber, a property of light emitted from the analyte-sensitive substance and (b) indicate data related to the detected property of the emitted light.

Some embodiments of the present disclosure provide a method including: (i) operating a body-mountable device that includes: (a) a flexible substrate that is configured to be mounted to a skin surface; (b) a sensor probe that is attached to the flexible substrate by a first end of the sensor probe and that has a second end that is configured to extend beneath the skin surface to contact interstitial fluid, wherein the sensor probe includes an optical fiber extending from the first end of the sensor probe to the second end of the sensor probe; (c) an analyte-sensitive substance that is disposed at the second end of the sensor probe and that has an optical property affected by an analyte in the interstitial fluid; (d) a light detector; and (e) one or more electronic components disposed on the flexible substrate; wherein the operating comprises: (1) obtaining, by the one more electronic components operating the light detector to detect light emitted from the analyte-sensitive substance via the optical fiber, data related to a property of the emitted light; and (2) indicating, by the one or more electronic components, the data related to the property of the emitted light.

Some embodiments of the present disclosure provide a method including: (i) depositing a solution proximate to a first end of an optical fiber, wherein the solution includes an analyte-sensitive substance and monomer units; and (ii) polymerizing the solution to form a polymer within which is disposed the analyte-sensitive substance and that is permeable to the analyte, wherein polymerizing the solution includes transmitting light via the optical fiber to expose the solution to the transmitted light.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4A is an aspect view of an example sensor that includes an optical fiber.

FIG. 4B is a cross-sectional view through the optical fiber of the example sensor of FIG. 4A.

FIG. 5A is an aspect view of an example sensor that includes an optical fiber.

FIG. 5B is an aspect view of an example sensor that includes an optical fiber.

DETAILED DESCRIPTION

Figure 1A:
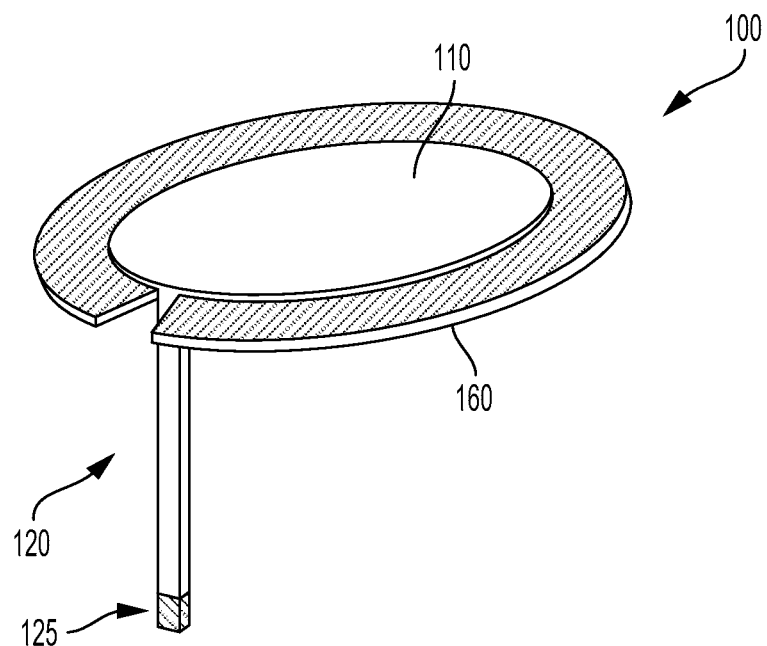
FIG. 1A is a top aspect view of an example body-mountable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Some embodiments of the present disclosure provide a body-mountable device configured to be mounted to a skin surface (e.g., to skin of the upper arm or abdomen of a person), with one or more sensors for quantitatively and qualitatively testing an analyte concentration in interstitial fluid (e.g., interstitial fluid within or beneath the skin) in situ and in real-time. The one or more sensors can include elements mounted on a sensor probe that is configured to penetrate the skin and that is attached to a flexible substrate of the device. Further, the flexible substrate is configured to be mounted to the skin surface (e.g., by use of glue, tape, dry adhesive, or other adhesive means). The flexibility of the flexible substrate could provide a sensing platform that minimally interferes with activities of a person to whom the sensing platform is mounted and/or that can be mounted to a person comfortably for protracted periods of time. Those of skill in the art will recognize that the sensing platform described herein may be provided in devices that could be mounted on a variety of portions of the human body to measure concentrations of an analyte in other fluids than interstitial fluid (e.g., to measure an analyte in a tear fluid, blood, saliva, or some other fluid or tissue of the body). Those of skill in the art will also recognize that the sensing platform described herein may be provided in devices that could be mounted in locations other than locations on a human body to measure concentrations of an analyte in a fluid proximate to the mounting location of the devices.

In some examples, a sensor of the sensing platform can be an optical sensor. For example, such a sensor could include an analyte-sensitive substance (e.g., a substance that specifically engages in a chemical reaction with the analyte, a substance that specifically binds to the analyte, or a substance that has a property that is related to the presence or concentration of the analyte) that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of the analyte-sensitive substance could be related to the presence, concentration, or some other property of the analyte. An optical sensor of the sensor platform could include a light emitter and/or a light detector configured to illuminate and/or to receive light emitted from the analyte-sensitive substance, respectively, in order to determine the optical property of the substance that is related to the analyte. In some examples, the sensor probe could include an optical fiber and the analyte-sensitive substance could be disposed on a distal end of such an optical fiber. In such examples, a light emitter and/or a light detector could be disposed at a proximal end of the optical fiber, such that the light emitter and light detector respectively illuminate and receive light from the analyte-sensitive substance via the optical fiber. In such examples, the light emitter and/or light detector could be disposed on the flexible substrate of the sensor platform (e.g., as part of the electronics disposed on the flexible substrate).

In some examples, the analyte-sensitive substance could be disposed on a surface of the sensing platform (e.g., on a distal surface of an optical fiber) and/or within a polymer, gel, or other layer that is permeable to the analyte and that is disposed on such a surface. Additionally or alternatively, a polymer, gel, or other layer that is permeable to the analyte could be disposed over the analyte-sensitive substance and/or other elements of the sensing platform to protect the elements of the sensor probe or according to some other application. In some examples, a permeability, thickness, or other properties of such an analyte-permeable layer could be specified to control a rate of diffusion of the analyte from interstitial fluid to element(s) of a sensor (e.g., to an analyte-sensitive substance disposed at the end of an optical fiber) or to some other element of the sensing platform. In some examples, a protective or other polymer layer could be a hydrogel, e.g., a hydrogel that includes units of 2-hydroxyethyl methacrylate.

The sensor probe can be configured to penetrate to a specified depth within the skin (e.g., to a depth within the dermis, to a subcutaneous depth) such that an analyte-sensitive substance disposed on the sensor probe (e.g., on a distal end of an optical fiber of the sensor probe) can be used to measure an analyte in fluid (e.g., interstitial fluid) at the specified depth. The sensor probe could be flexible or rigid; in some examples, the sensor probe could comprise an elongate extension of the flexible substrate material. The sensor probe could be configured to pierce the skin (e.g., could be sufficiently rigid and/or sharpened such that the sensor probe can be driven into the skin). Additionally or alternatively, the sensor probe could be configured to pierce and/or penetrate the skin in combination with an insertion device. For example, the sensor probe could be configured to be mounted within the channel of a half-needle or to some other means for piercing the skin; the half needle or other piercing means could be used to pierce the skin and to subsequently retract, leaving the sensor probe in place penetrating the skin. One or more sensors or elements of sensors (e.g., analyte-sensitive substances) could be disposed at the end of such a sensor probe and/or at one or more additional locations along the length of such a sensor probe.

A sensing platform can include a power source, electronics, and an antenna all disposed on the flexible substrate configured to be mounted to a skin surface. The electronics can operate one or more sensors (e.g., a sensor disposed at the distal end of a sensor probe, an optical sensor configured to detect an optical property of an analyte-sensitive substance disposed at the distal end of a sensor probe) to perform measurements of an analyte (e.g., to measure the concentration of the analyte in interstitial fluid within or beneath the skin). The electronics could additionally operate the antenna to wirelessly communicate the measurements from the sensor(s) or other information to an external reader or some other remote system via the antenna. One or more of the power source, antenna, electronics, or other components of the sensing platform could be flexible; for example, the power source could include a thin, flexible lithium ion battery.

Some embodiments of the present disclosure further include a user interface configured to receive inputs from a user (e.g., a user to whose body the device is mounted)

and/or present outputs to the user to provide some application(s) of the body-mountable device. Such user-interface elements (e.g., displays, sensors, buttons) could be flexible and/or mounted to the flexible substrate of the sensing platform. In some examples, the user interface could provide means for changing or setting an operational state of the sensing device and/or for causing the performance of some function by the sensing platform. For example, the user interface could provide means for a user to cause the sensing platform to perform a measurement of the physiological property using the sensor, to set the sensing platform into a sleep or other low-power state, to set a rate of operation of the sensor to detect the physiological property, or to control some other aspect of operation or function of the sensing platform. In some examples, the user interface could provide means for inputting calibration or other data to the sensing platform, e.g., for inputting calibration data related to the operation of the sensor to detect the physiological property. Additionally or alternatively, the user interface could provide means for inputting information about the state of a user of the sensing platform, e.g., to indicate a physical or mental state of the user, to indicate an activity of the user, to indicate that the user has eaten a meal or taken a drug, or to indicate some other information. The user interface could provide means for indicating information to a user, for example, information about the operation of the sensing platform (e.g., battery charge state, an amount of free memory), detected physiological properties (e.g., a blood glucose level detected using the sensor), or some other information available to the sensing platform.

The sensing platform can be powered via one or more batteries in the sensing platform and/or by energy from an external source. In some examples, the one or more batteries could be flexible and disposed on the flexible substrate to allow for flexibility of the overall sensing platform and/or of elements of the sensing platform that are able to be mounted to skin (e.g., to provide greater comfort and/or to minimize effect on user activities when mounted to skin of a user). Such flexible batteries could include flexible lithium ion batteries. Batteries of a sensing platform as described herein could be single-use or could be rechargeable. Rechargeable batteries could be recharged by power provided by radio frequency energy harvested from an antenna disposed on the flexible substrate. The antenna can be arranged as a loop of conductive material with leads connected to the electronics. In some embodiments, such a loop antenna can also wirelessly communicate the information (e.g., measurements of the analyte made using a sensor of the sensing platform) to an external reader (e.g., to a cellphone) by modifying the impedance of the loop antenna so as to modify backscatter radiation from the antenna. Additionally or alternatively, the sensing platform could include a chip, dipole, or other type of antenna for transmitting and/or reflecting RF energy to indicate information to an external reader. Further, such antennas could be used to transfer additional information, e.g., to indicate a temperature, light level, or other information detected by the sensing platform, to receive commands or programming from an external device, or to provide some other functionality.

It should be understood that the above embodiments, and other embodiments described herein, are provided for explanatory purposes, and are not intended to be limiting.

II. EXAMPLE FLEXIBLE BIOSENSOR PLATFORM

Figure 1B:
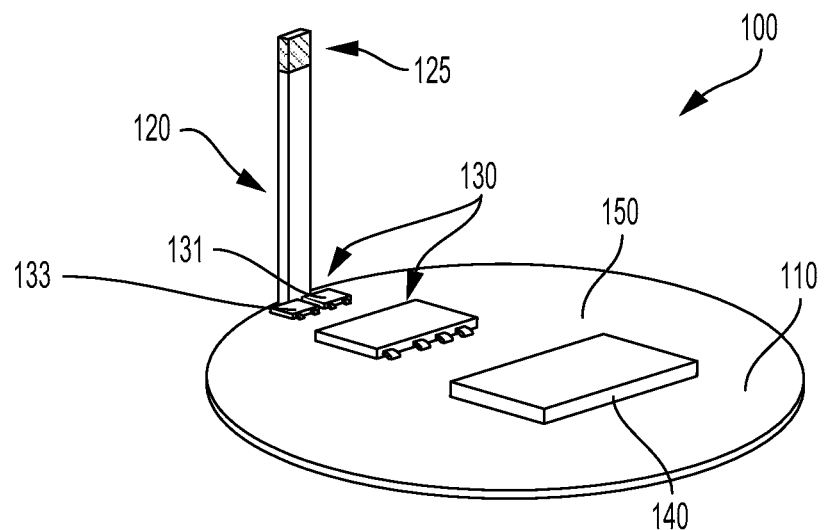
FIG. 1B is a bottom aspect view of the example body-mountable device shown in FIG. 1A.

FIG. 1A is a top view of an example body-mountable sensing platform 100. FIG. 1B is a bottom view of the example body-mountable sensing platform shown in FIG. 1A. It is noted that relative dimensions in FIGS. 1A and 1B are not necessarily to scale, but have been rendered for purposes of explanation only in describing the arrangement of the example body-mountable sensing platform 100. The body-mountable device 100 is formed of a flexible substrate 110 shaped (as an illustrative example) as a circular disk. A sensor probe 120 extends from the flexible substrate 110 and is configured to penetrate a skin surface (e.g., to penetrate into skin of the upper arm or abdomen of a human body). An analyte-sensitive substance 125 is disposed at a distal end of the sensor probe 120. The analyte-sensitive substance 125 has an optical property (e.g., a color, a reflectivity, a fluorescence intensity, a fluorescence lifetime) that is related to a property (e.g., a concentration) of an analyte (e.g., glucose) in fluids to which the analyte-sensitive substance is exposed. Measurement of such an optical property of the analyte-sensitive substance 125 could provide for determination of the concentration or other related property of the analyte in interstitial or other fluids under and/or within the skin when the sensor probe 120 penetrates the skin. An adhesive layer 160 is provided to mount the flexible substrate 110 to a skin surface (the adhesive layer 160 is not shown in FIG. 1B, to allow illustration of elements of the body-mountable sensing platform 100 that are disposed on the bottom surface 150 of the flexible substrate 110).

The body-mountable sensing platform 100 additionally includes electronics 130 disposed on the flexible substrate 110 and configured to provide various applications of the sensing platform 100 including, e.g., using the analyte-sensitive substance 125 to detect the analyte, recording information about the analyte in a memory of the electronics 130, and communicating information about the analyte (e.g., by using an antenna to wirelessly indicate such information) to an external system. The electronics 130 include a light emitter 131 and a light detector 133 configured to respectively illuminate and the detect light emitted from the analyte-sensitive substance 125 via an optical fiber (not shown) of the sensor probe 120. The antenna (not shown) could be configured as a loop antenna on bottom surface 150 (e.g., encircling electronics 130), or the antenna could be configured as a chip antenna or some other configuration. A battery 140 is provided to power the body-mountable sensing platform 100 (e.g., to power the electronics 130). Components (e.g., antennas, batteries, electronics, user interface elements) could additionally or alternatively be disposed on the top surface of the flexible substrate 110 (i.e., the surface of the flexible substrate 110 opposite the bottom surface 150).

Using the analyte-sensitive substance 125 to detect the analyte includes detecting the optical property of the analyte-sensitive substance 125 that is related to the analyte (e.g., related to the concentration of the analyte in a fluid to which the analyte-sensitive substance 125 is exposed). The optical property could be a color, an absorbance spectrum, a reflectance spectrum, an excitation spectrum, an emission spectrum, a reflectivity, a fluorescence intensity, a fluorescence lifetime, or some other optical property of the analyte-sensitive substance 125 that is related to the analyte and that can be optically detected. Such detection could include operating the light detector 133 to detect an intensity, wavelength, spectral profile, a time-dependence, or other properties of light emitted from (e.g., reflected by, scattered by, fluorescently emitted from, or otherwise emitted from) the analyte-sensitive substance 125 and transmitted to the light detector 133 via the optical fiber of the sensor probe 120. Detection can further include operating the light emitter 131 to emit light having a specified intensity, wavelength, spectral profile, polarization, or other properties to illuminate the analyte-sensitive substance 125 by transmitting such illumination via the optical fiber of the sensor probe 120.

In a particular example, the analyte-sensitive substance could include a fluorophore functionalized with an analyte-sensitive moiety (e.g., a boronic acid moiety for selective interaction with glucose) such that a fluorescence intensity (i.e., an intensity of light fluorescently emitted at one or more emission wavelengths in response to illumination by light having a specified intensity at one or more excitation wavelengths) is related to interaction between (e.g., binding of) the analyte-sensitive moiety and the analyte. In such an example, the fluorescence intensity of the analyte-sensitive substance could be detected by illuminating the analyte-sensitive substance 125 using the light emitter 131 and detecting an intensity of light responsively emitted from the analyte-sensitive substance 125 using the light detector 133. The concentration of the analyte could then be determined based on the detected fluorescence intensity.

The flexible substrate 110 is configured to be mounted to a skin surface. In the example shown in FIGS. 1A and 1B, this includes a layer of adhesive 160 being provided to adhere the flexible substrate 110 to a skin surface. Additional or alternative means could be provided to mount the flexible substrate 110 to a skin surface. For example, a liquid or gel adhesive could be applied to the skin surface and/or to the flexible substrate 110 to mount the flexible substrate 110 to the skin surface. The flexible substrate 110 could be placed on the skin surface and secured using tape or other adhesives. In some examples, the body-mountable sensing platform 100 could include a dry adhesive configured to removably mount the flexible substrate 110 to a skin surface. Other means for mounting the flexible substrate 110 or other elements of the body-mountable sensing platform 100 to a skin surface or to other elements or aspects of a living body are anticipated. Further, in some embodiments, a body-mountable sensing platform 100 could be provided that is configured to be emplaced proximate a target fluid (e.g., interstitial fluid, synovial fluid, blood, tears, saliva, mucus) without mounting to a skin surface or other tissue surface. For example, a body-mountable sensing platform 100 as described herein could be configured to be placed between the teeth and cheek of a living body, on the eye of a living body, or at some other location of a living body without being mounted to a particular tissue surface.

The flexible substrate 110 can have a thickness, shape, composition, and/or other properties specified such that the flexible substrate 110 can be mounted to a skin surface of a living body and further such that such mounting minimally interferes with activities of the living body (e.g., motions of the living body). This could include the flexible substrate 110 being sufficiently flexible that mounting of the flexible substrate 110 to the skin surface causes a minimum of discomfort. The flexible substrate 110 could be composed of polyimide or some other flexible polymeric or other material. The flexible substrate could have a thickness less than approximately 100 microns. Further, the flexible substrate 110 could have a size specified to minimally interfere with activities of the living body. For example, the flexible substrate 110 could have size (e.g., a diameter of a circular portion, as illustrated in FIGS. 1A and 1B) less than approximately 11 millimeters. Diameter and thickness values are provided for explanatory purposes only. Further, the shape of the flexible substrate 110 could be different from that illustrated in FIGS. 1A and 1B or elsewhere herein; for example, the flexible substrate 110 could have an elongate shape, a square or rectangular shape, or some other shape according to an application. For example, the flexible substrate 110 could have an elongate shape to provide sufficient area for disposition of electronics, batteries, antennas, or other components on the flexible substrate 110 while minimally impeding motion and/or deformation of the skin surface to which the flexible substrate 110 is mounted (e.g., by being formed and/or mounted to the skin surface such the orientation of the elongate shape of the flexible substrate 110 is perpendicular to a direction of strain of the skin surface).

One or more surfaces of the flexible substrate 110 (e.g., the bottom surface 150) could be used as a platform for mounting electronics such as chips (e.g., via flip-chip mounting) and for patterning conductive materials (e.g., via deposition techniques) to form electrodes, antenna(e), and/or connections. The composition of the flexible substrate 110 could be chosen to allow for the formation and/or disposition of such elements of the body-mountable sensing platform 100. For example, the flexible substrate 110 could be composed of polyimide or some other polymeric and/or metallic material(s) such that metal contacts, traces, and interconnects can be patterned directly on the surface of the flexible substrate 110 (e.g., by sputtering, CVD, or some other deposition process) and/or on a coating or layer formed on one or more surfaces of the flexible substrate 110. Further, such patterned structures and/or other elements disposed on the flexible substrate 110 (e.g., electronics 130 including a light emitter 131 and light detector 133, battery 140, antennas) could, in combination with the flexible substrate 110, have a thickness or other property specified to provide the overall body-mountable sensing platform 100 with flexibility. For example, the flexible substrate 110 in combination with electronics 130 and battery 140 disposed thereon could have a thickness less than approximately 0.5 millimeters.

The electronics 130 disposed on the flexible substrate 110 could include a variety of devices. For example, the electronics 130 could include an antenna (e.g., a chip antenna), a microcontroller, amplifiers, light emitters (e.g., 131), light detectors (e.g., 133), temperature sensors, transmitters, radios, transceivers, or some other component or components. Such components can be mounted to and/or electrically connected via interconnects or traces patterned on the flexible substrate 110. Further, antennas, electrodes, capacitors, resistors, or other components could be formed from such traces or other interconnects formed on the surface of the flexible substrate 110. The electronics 130 can include logic elements configured to operate the light detector 133 and/or light emitter 131 to detect an analyte (e.g., by detecting an optical property of the analyte-sensitive substance 125 that is related to the analyte), an antenna (e.g., a loop, dipole, or other type of antenna formed on the flexible substrate 110, a chip antenna disposed on the flexible substrate 110) to wirelessly indicate information (e.g., concentration levels) about the detected analyte, and/or to provide other functions. A loop, dipole, or other type of antenna can be one or more layers of conductive material patterned on a surface (e.g., 150) of the flexible substrate 110 to form one or more specified conductive shapes (e.g., a ring, a spiral, a curved or straight line, an elliptical or rectangular patch, a fractal). Electrical interconnects (e.g., traces), antennas, and/or conductive electrodes (e.g., for an electrochemical analyte sensor, etc.) can be formed from conductive materials patterned on the flexible substrate 110 by a process for precisely patterning such materials, such as deposition, lithography, etc. The conductive materials patterned on the flexible substrate 110 can be, for example, gold, platinum, palladium, titanium, carbon, aluminum, copper, silver, silver-chloride, conductors formed from noble materials, metals, combinations of these, etc.

The sensor probe 120 is an elongate element of the body-mountable sensing platform 100 that is configured to penetrate a skin surface such that the analyte-sensitive substance 125 located at the distal end of the sensor probe 120 is in contact with a fluid (e.g., interstitial fluid, blood) containing an analyte of interest (e.g., glucose) when the sensor probe 120 is penetrating the skin. For example, the sensor probe 120 could be more than approximately 2 millimeters long. The sensor probe 120 could have a length or other properties specified such that, when the sensor probe 120 penetrates skin and/or the flexible substrate 120 is mounted to a skin surface, a sensor or element(s) thereof (e.g., 125) or other element(s) disposed on the sensor probe 120 contact tissue at a specified depth within the skin (e.g., tissue of the dermis of the skin, subcutaneous tissue). For example, the sensor probe 120 could have a length between approximately 500 microns and approximately 6000 microns. Further, the sensor probe 120 could have one or more dimensions specified to provide sufficient area for electrodes or other elements disposed on the sensor probe 120, to minimally interfere with the skin (e.g., by requiring a minimal incision or other alteration of the skin to provide for penetration of the sensor probe 120), or according to some other application. For example, the sensor probe 120 could have a width between approximately 25 microns and approximately 400 microns.

The sensor probe 120 could be composed of a variety of materials and elements formed by a variety of processes. The sensor probe 120 includes an optical fiber (not shown) configured to transmit light emitted from the analyte-sensitive substance 125 to the light detector 133 and to transmit light produced by the light emitter 131 from the light emitter 131 to the analyte-sensitive substance 125. This can include the analyte-sensitive substance 125 being disposed at a distal end of the optical fiber (e.g., deposited in a layer on the end of the optical fiber, disposed within a polymeric material disposed at and/or attached to the distal end of the optical fiber, disposed within material of the distal end of the optical fiber) and the proximal end of the optical fiber being optically coupled to the light emitter 131 and light detector 133 (e.g., by proximity, by lenses, mirrors, waveguides, optically clear adhesives, or other optical elements). The optical fiber could include a core having a first refractive index and a layer of cladding surrounding the core and having a second refractive index such that light transmitted within the optical fiber experiences total internal reflection. The optical fiber could include more layers or other structures configured to provide for transmission of light between ends of the optical fiber. The optical fiber could be composed of glass, plastics, or other materials.

The sensor probe 120 could include a backing or substrate (e.g., an elongate extension of the flexible substrate 110) to which the optical fiber is mounted (e.g., to provide support to the optical fiber, to provide secure mechanical connection between the optical fiber and the flexible substrate 110, to provide means for piercing skin to allow the sensor probe 120 to penetrate the skin). Alternatively, the sensor probe 120 could consist essentially of the optical fiber and analyte-sensitive substance 125 disposed on a distal end thereof. The sensor probe 120 could be composed of flexible materials (e.g., polyimide, glass or polymer optical fiber(s)) or a relatively inflexible material; further, a thickness, width, shape, or other properties of the sensor probe 120 could be specified to provide a degree of flexibility or inflexibility. For example, a flexible sensor probe 120 could have a width between approximately 25 microns and approximately 400 microns and/or a thickness less than approximately 100 microns. In some examples, the sensor probe 120 could be partially formed from the same material as the flexible substrate 110; i.e., the sensor probe 120 could include an optical fiber mounted to an elongate portion of the flexible substrate 110 that extends from a portion of the flexible substrate 110 that is configured to be mounted to a skin surface and/or on which electronics 130 or other components are disposed. Alternatively, the sensor probe 120 could be attached to the flexible substrate 110. For example, the sensor probe 120 could include an optical fiber, flexible element(s) (e.g., an elongate piece of polyimide or other polymeric or metallic substance), wire(s), elongate pieces of shaped silicon, or other elements adhered, welded, bonded, or otherwise attached to the flexible substrate 110. Alternatively, such sensor probes could be used for other applications and/or in combination with components or devices other than a flexible substrate (e.g., 110) as described herein.

The sensor probe 120 could be configured to pierce skin to allow the sensor probe 120 to penetrate the skin and dispose the analyte-sensitive substance 125 in contact with interstitial or other fluids within the skin. For example, the sensor probe 120 could be sharpened, could include one or more rigid materials to facilitate application of force to the sensor probe 120 to pierce the skin (e.g., stainless steel tubes, rods, sheets, and/or needles), or could be otherwise configured to pierce skin. In some examples, the sensor probe 120 could include materials having a stiffness or some other property that changes to allow the sensor probe 120 to be used to pierce the skin during a first period of time and subsequently to become less rigid or to change some other property according to an application. In some examples, the sensor probe 120 could include a material configured to initially have a high rigidity, to allow for piercing of skin, and to soften when the sensor probe penetrates the skin for a period of time. For example, the sensor probe 120 could include a piece of poly-2-hydroxyethyl methacrylate (poly-HEMA) or some other hydrogel configured to soften by absorbing water (e.g., from interstitial fluid) once the sensor probe 120 has penetrated the skin. In another example, the sensor probe 120 could include a stiff material that is configured to wholly or partially dissolve into and/or be absorbed by the skin (e.g., polylactic acid (PLA)). Additionally or alternatively, the sensor probe 120 could be inserted into skin by another device that is configured to pierce the skin, or into an incision into the skin formed by another device. For example, the sensor probe 120 could be configured to be mounted within the channel of a half-needle of a device (e.g., a device configured to insert the sensor probe 120 into skin and/or to mount the flexible substrate 110 to a skin surface) such that the half-needle could pierce the skin and subsequently be refracted, leaving the sensor probe 120 in place penetrating the skin.

Note that the depiction of a body-mountable sensor platform 100 having a single sensor probe 120 that includes an optical fiber on a distal end of which a single analyte-sensitive substance 125 is disposed is intended as a non-limiting, illustrative example. A particular sensor probe of a body-mountable sensing platform could include additional analyte-sensitive substances (e.g., substances sensitive to the same analyte and/or to different analytes) disposed at different locations on the particular sensor probe at distal ends of respective different optical fibers of the sensor probe. For example, a particular sensor probe could include a plurality of optical fibers having respective different lengths and at the distal ends of which are disposed respective analyte-sensitive substances such that the respective analyte-sensitive substances are disposed along the length of the particular sensor probe to allow for detection of some property of skin (e.g., a concentration of an analyte within the skin) at a variety of depths within the skin. Additionally or alternatively, two or more different analyte-sensitive substances (e.g., sensitive to respective different analytes) could be disposed at the distal end of a single optical fiber and optical properties of the two or more different analyte-sensitive substances could be detected by illuminating and/or detecting light emitted from the analyte-sensitive substances via the optical fiber.

A body-mountable sensor platform could include more than one sensor probe. The sensor probes could have respective widths, lengths, thicknesses, analyte-sensitive substances, analyte-sensitive substance locations, or other properties. Further, a body-mountable sensing platform could include an analyte-sensitive substance or other element(s) of sensors that are not disposed at a distal end or other locations on a sensor probe. For example, one or more sensors or element(s) of sensors (e.g., an analyte-sensitive substance) could be disposed on a flexible substrate (e.g., 110) or other element(s) of such a body-mountable sensing platform.

While not illustrated in FIG. 1A or 1B, a body-mountable sensing platform (e.g., 100) as described herein could include one or more user interface elements configured to receive user input (e.g., from a user whole skin the sensor probe 120 is penetrating and whose skin surface the flexible substrate 110 is mounted to) and/or to indicate information. A body-mountable sensing platform could include lights (e.g., discrete LEDs), displays (e.g., flexible OLED displays), vibration motors, electrohaptic stimulators, or other means for indicating information to a user. Such indicated information could include information about a detected analyte (e.g., a detected concentration of the analyte), information about the status of the body-mountable sensing platform (e.g., battery charge status, free memory space status), alerts (e.g., alerts that a concentration of the analyte is within/outside of a specified range, alerts that a particular health state has been detected, alerts that a user should perform some medical task and/or seek medical attention), or some other information. A body-mountable sensing platform could include buttons, capacitive touch-sensing elements configured to detect touches and/or gestures, temperature sensors configured to detect touches, or other means for detecting input from a user. Such input could include instructions to perform some task (e.g., to operate the light detector 133 and/or light emitter 131 to detect the analyte), to change an operational state (e.g., to start and/or stop regular detection of the analyte, to change a frequency at which the analyte is detected), to indicate a personal and/or health state of a user (e.g., to indicate that the user is experiencing nausea, lightheadedness, etc.), to indicate that an event has occurred (e.g., that the user has administered/been administered a drug), or some other input/instructions to the body-mountable sensing platform.

A variety of sensor probes configured to penetrate skin, and devices (e.g., body-mountable sensing platforms) including such sensor probes, are described herein. Such sensor probes could be configured and/or operated to penetrate skin through a pre-existing cut, puncture, incision, or other entry through the surface of the skin into tissue (e.g., dermal tissue, subcutaneous tissue) containing an analyte-containing fluid of interest (e.g., interstitial fluid). Such a pre-existing entry could be formed for the purpose of inserting the sensor probe by a lancet, needle, or other instrument configured to pierce the skin. Additionally or alternatively, the sensor probe and/or some other element of a body-mountable sensing platform could be configured to pierce the skin, e.g., by including rigid elements, by including a sharpened end, or by being configured in some other way to allow piercing of the skin. In some examples, the sensor probe (and body-mountable sensing platform, in embodiments wherein the sensor probe is an element of such a sensing platform) could be removably mounted to an insertion device configured to pierce the skin in combination with the sensor probe and to retract leaving the sensor probe in place (i.e., penetrating the skin).

Figure 2B:
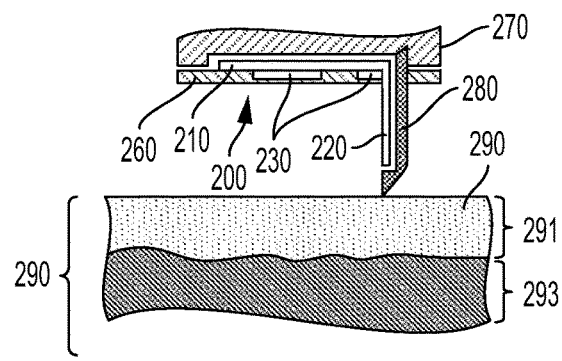
FIG. 2B is a cross-sectional view of the body-mountable device and insertion device of FIG. 2A, positioned proximate to skin of a living body.
Figure 2A:
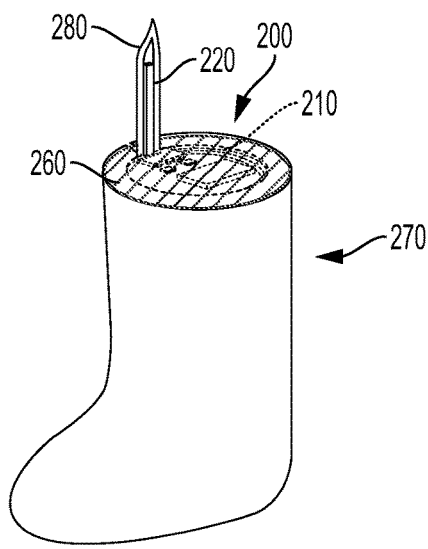
FIG. 2A is an aspect view of an example body-mountable device removably mounted to an example insertion device.

FIG. 2A illustrates an example body-mountable sensing platform 200 removably mounted to an example insertion device 270. The body-mountable sensing platform 200 includes a flexible substrate 210, a sensor probe 220 attached to the flexible substrate 210, and an adhesive layer 260 configured to adhere the flexible substrate 210 to a skin surface. The sensor probe 220 is configured to penetrate the skin and includes an optical fiber (not shown) to a distal end of which an analyte-sensitive substance is disposed (not shown). The analyte-sensitive substance has an optical property that is related to an analyte in fluid to which the analyte-sensitive substance is exposed. Electronics 230 disposed on the flexible substrate 210 include a light detector and/or light emitter configured to detect an analyte (e.g., to measure a concentration of glucose) in a fluid within the skin (e.g., in interstitial fluid) when the sensor probe 220 penetrates the skin by detecting the optical property of the analyte-sensitive substance. The light detector and/or light emitter are optically coupled to a proximal end of the optical fiber (e.g., by proximity to the optical fiber, by an optically clear adhesive, by an optical waveguide, mirror, lens, or other optical elements) such that illumination of and/or detection of light emitted from the analyte-sensitive substance include transmission of light via the optical fiber.

The sensor probe 220 is coupled to a needle 280 of the insertion device 270. The needle 280 is a half-needle; that is, the needle 280 includes a channel along the length of the needle 280 in which the sensor probe 220 is disposed. The needle 280 is configured to pierce skin such that the needle 280 and the coupled sensor probe 220 penetrate the skin. That is, the needle is sufficiently rigid and/or has an end that is sufficiently sharp that force can be applied to the insertion device 270 such that the needle 280 pierces the skin. The insertion device 270 can then be moved away from the skin, retracting the needle 280 while the sensor probe 220 remains inserted in (i.e., penetrating) the skin and the flexible substrate 210 remains mounted on the skin surface.

Figure 2C:
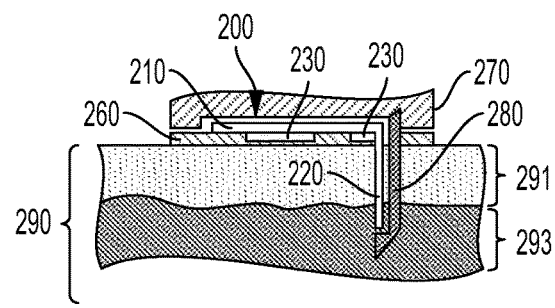
FIG. 2C is a cross-sectional view of the body-mountable device, insertion device, and skin of a living body of FIG. 2B, showing the body-mountable device and insertion device penetrating the skin.
Figure 2D:
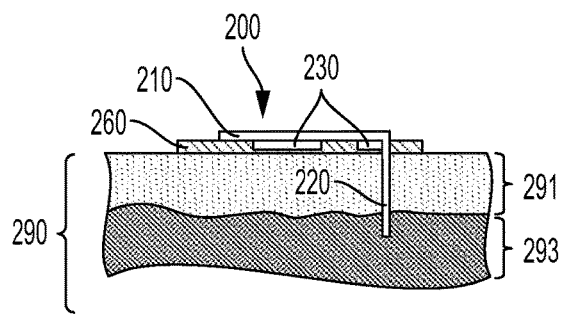
FIG. 2D is a cross-sectional view of the body-mountable device, insertion device, and skin of a living body of FIG. 2B, showing the body-mountable device penetrating the skin and the insertion device retracted from the skin.

FIGS. 2B-2D show, in cross-section, the process of using the insertion device 270 to pierce skin 290. The skin 290 includes an epidermal layer 291 and a dermal layer 293. FIG. 2B shows the body-mountable sensing platform 200 removably mounted to the insertion device 270 such that the sensor probe 220 of the sensing platform 200 is coupled to the needle 280 of the insertion device (that is, in this example, that the sensor probe 220 is disposed within a channel of the needle 280). As shown in FIG. 2B, the insertion device 270 and sensing platform 200 removably mounted thereto are disposed proximate the skin 290, but have not yet pierced and/or penetrated the skin 290.

FIG. 2C shows the insertion device 270 and sensing platform 200 after the needle 280 (and sensor probe 220 coupled thereto) has been inserted into the skin 290 (i.e., the needle 280 has pierced the skin). Further, the flexible substrate 210 has been mounted, via the adhesive action of the adhesive layer 260, to the skin 290 surface. The sensor probe 220 penetrates the skin 290 such that the distal end of the sensor probe 220 is located in the dermal layer 293 of the skin 290 (e.g., such that a sensor disposed on the end of the sensor probe 220 could detect an analyte in interstitial or other fluids present in the dermal layer 293). FIG. 2D shows the sensing platform 200 after the needle 280 of the insertion device 270 has been retracted. The sensor probe 220 continues to penetrate the skin 290 such that the distal end of the sensor probe 220 is located in the dermal layer 293 of the skin 290.

Note that the illustrated insertion device 270 and sensing platform 200 and use thereof to pierce and/or penetrate the skin 290, are intended as non-limiting illustrative examples of such devices and methods. An insertion device 270 and/or sensing platform 200 could have different shapes, include different components and/or elements, be configured different, and/or differ in some other way as will be clear to one of skill in the art. For example, the insertion device could consist of a disk to which a half-needle or other penetrating means are attached and to which a body-mountable sensing platform could be removably mounted. In some examples, the insertion device 270 could be configured to provide some additional functionality, e.g., could be configured to receive communications from the sensing platform (e.g., to receive information related to the detected analyte), to recharge a sensing platform, to activate a sensing platform, or to provide some other functionality. In some examples, an insertion device could include a driving mechanism (e.g., a spring-loaded mechanism, a servomechanism including one or more solenoids, motors, or other electromechanical actuators) configured to drive a needle (and sensor probe coupled thereto) into skin (e.g., to a specified depth within the skin, at a sufficiently high speed to minimize user discomfort). In some examples, the needle 280 could be retractable into the insertion device 270 for safety.

Note that the mounting of body-mountable sensing platforms to skin surfaces of living bodies, and the penetration of such skin by sensor probes of sensing platforms, are intended as non-limiting illustrative examples of devices and methods described herein. Such devices and systems could be used to detect analytes in other fluids in other tissues by penetrating such other tissues with sensor probes and/or mounting flexible substrates to surfaces of such tissues. For example, sensor probes, flexible substrates, and/or sensing platforms as described herein could be used to detect an analyte within a mucosal epithelium (e.g., within the mucosa of a mouth, nose, or other mucosa of a living body). Additionally or alternatively, sensor probes, flexible substrates, and/or sensing platforms as described herein could be used to detect analytes in a variety of fluids without penetrating tissues (e.g., to detect an analyte in a tissue present in a volume of a living body, e.g., to detect an analyte in peritoneal fluid by disposing a sensing-platform as described herein within the peritoneal cavity of a living body). Further, systems and devices as described herein could be used to detect analytes in fluids of an animal and/or plant body, and/or to detect an analyte in a natural environment (e.g., a stream, a lake) and/or an artificial environment (e.g., fluids of a pharmaceutical process, fluids of a water treatment process, fluids of a food processing process).

An analyte-sensitive substance disposed at a distal end of an optical fiber (e.g., an optical fiber of a sensor probe) or at some other location of a body-mountable sensing platform as described herein could include a variety of substances configured in a variety of ways. In some examples, such analyte-sensitive substances could include one or more substances that selectively interact with an analyte. For example, such substances could include proteins, enzymes, aptamers, DNA, RNA, nano-structures, antibodies, reagents, nano-structured surfaces, or other substances configured to selectively bind to, catalyze a reaction of, or otherwise selectively interact with an analyte of interest. Such an analyte-sensitive substance could be disposed on a surface of a sensing platform (e.g., on a distal surface of an optical fiber, on some other surface of a sensor probe and/or flexible substrate) and/or within a polymer, gel, or other layer that is permeable to the analyte and that is disposed on such a surface.

In some examples, an analyte-sensitive substance could be disposed on a surface of a sensing platform (e.g., on a distal surface of an optical fiber) by crosslinking the substance on the surface (e.g., using glutaraldehyde to crosslink the analyte-sensitive substance). In some examples, an analyte-sensitive substance can be disposed within a polymer layer or other formed shape formed on a surface of a sensing platform. Such a polymer layer can be permeable to the analyte and contain a reagent that selectively reacts with the analyte to create a reaction product that can be sensed directly by a fluorophore or some other substance that selectively interacts with the reaction product and that has an optical property related to the reaction product. In some examples, the polymer layer that contains the analyte-sensitive substance is a hydrogel that includes 2-hydroxyethyl methacrylate units. Such a hydrogel could contain additional polymer units or other chemicals to adjust a permeability of the hydrogel to the analyte, to bind the analyte-sensitive substance or other related substances within the hydrogel, in increase a degree of crosslinking of the hydrogel, or to specify one or more other properties of the hydrogel. For example, such a hydrogel could additionally include di(ethylene glycol) dimethacrylate units.

The optical property of the analyte-sensitive substance could be related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of the analyte-sensitive substance could be related to the presence, concentration, or some other property of the analyte.

A light detector configured to detect light emitted from the analyte-sensitive substance (e.g., light scattered by, reflected by, chemiluminescently emitted by, fluorescently emitted by, or otherwise emitted by the analyte-sensitive substance) could be configured to detect an intensity, a polarity, a degree of polarization, a wavelength, a spectral line width, a spectrum, or some other properties of the emitted light. Such a light detected could include one or more photodiodes, phototransistors, charge-coupled devices, active pixel sensors, polarization filters, color filters, diffraction gratings, lenses, mirrors, or other elements configured to provide for detection and/or determination of properties of light emitted from the analyte-sensitive substance and transmitted to the light detector via an optical fiber. Conversely, a light emitter configured to illuminate the analyte-sensitive substance via the optical fiber could be configured to emit light having a specified wavelength, spectral profile, coherence length, polarization direction or degree, or other properties. Such a light emitter could include one or more LEDs, lasers, lenses, filters, volume holographic gratings, or other light-emitting and/or optical elements configured to provide for the illumination of the analyte-sensitive substance.

In some examples, a polymer, gel, or other layer that is permeable to the analyte could be disposed over one or more components of the sensing platform (e.g., over an analyte-sensitive substance disposed on a distal end of an optical fiber) and/or other elements of a sensing platform to protect the elements of the sensing platform or according to some other application. In some examples, a permeability, thickness, or other properties of such an analyte-permeable layer (and/or of a similar layer containing and/or composed of an analyte-sensitive substance) could be specified to control a rate of diffusion of the analyte from interstitial fluid to an analyte-sensitive substance or to some other element of the sensing platform (e.g., to an analyte-sensitive electrode or some other element of the sensing platform). In some examples, a protective or other polymer layer could be a hydrogel, e.g., a hydrogel that includes units of 2-hydroxyethyl methacrylate and/or units of di(ethylene glycol) dimethacrylate.

III. EXAMPLE ELECTRONICS OF A FLEXIBLE BIOSENSOR PLATFORM

Figure 3:
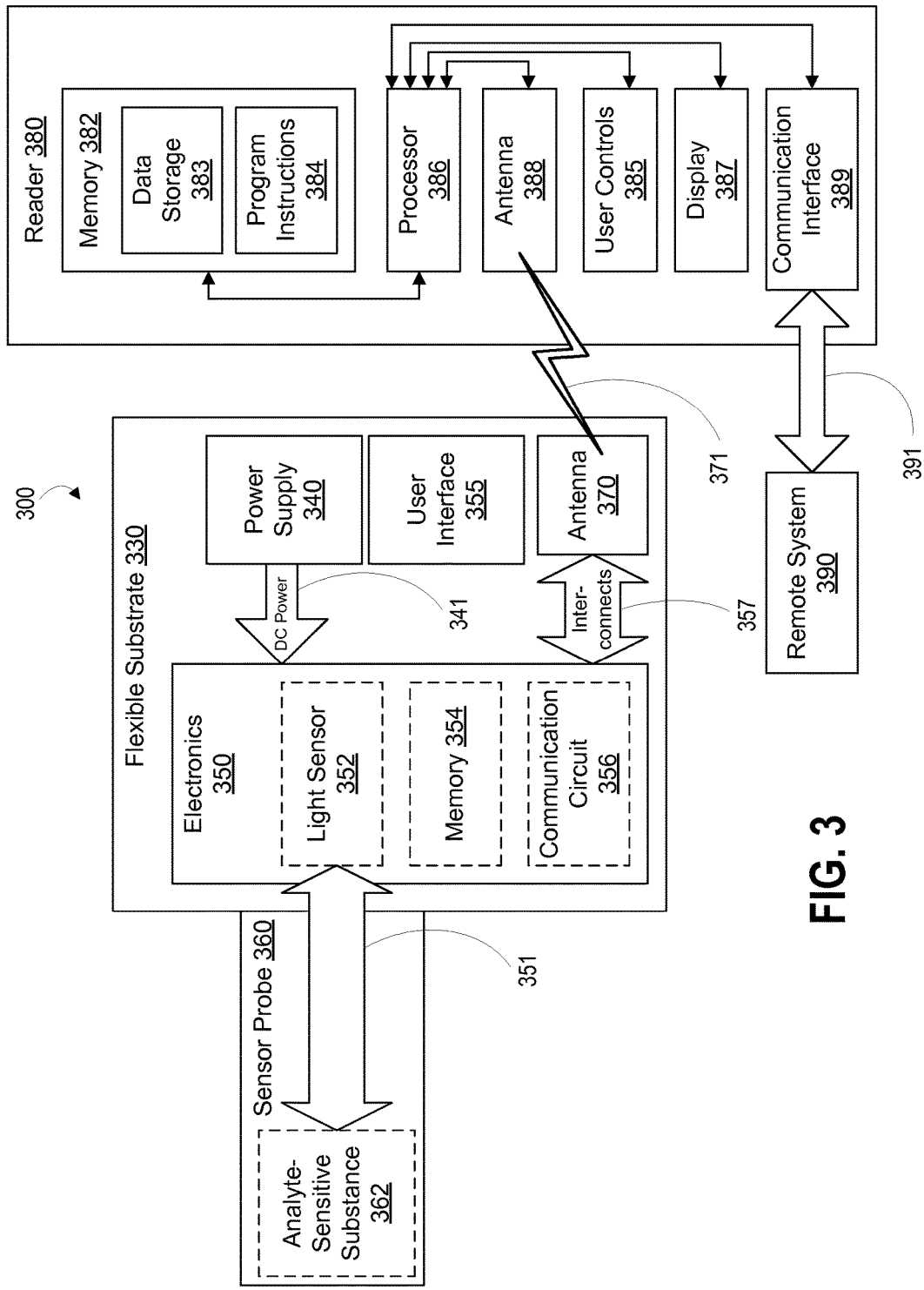
FIG. 3 is a block diagram of an example system that includes a body-mountable device in wireless communication with an external reader.

FIG. 3 is a block diagram of a system that includes a body-mountable sensor platform 300 in wireless communication with an external reader 380. The body-mountable sensor platform 300 includes a flexible substrate 330 that is made of a flexible polymeric or metallic material formed to be mounted to a skin surface. The flexible substrate 330 provides a mounting surface for a power supply 340, electronics 350, user interface 355, and a communication antenna 370. The power supply 340 supplies operating voltages to the electronics 350 and/or other elements of the sensing platform 300. The antenna 370 is operated by the electronics 350 to communicate information to and/or from the body-mountable sensing platform 300. The antenna 370, the electronics 350, user interface 355, and the power supply 340 can all be situated on the flexible substrate 330.

The flexible substrate 330 can have a thickness, shape, composition, and/or other properties specified such that the flexible substrate 330 can be mounted to a skin surface of a living body and further such that such mounting minimally interferes with activities of the living body (e.g., motions of the living body). This could include the flexible substrate 330 being sufficiently flexible that mounting of the flexible substrate 330 to the skin surface causes a minimum of discomfort. The flexible substrate 330 could be composed of polyimide or some other flexible polymeric or other material. One or more surfaces of the flexible substrate 330 could be used as a platform for mounting components or elements of the antenna 370, the electronics 350, user interface 355, and the power supply 340 such as chips (e.g., via flip-chip mounting) and conductive materials (e.g., via deposition techniques) that form electrodes, antenna(e), and/or connections. The composition of the flexible substrate 330 could be specified such that metal contacts, traces, and interconnects can be patterned directly on the surface of the flexible substrate 330 (e.g., by sputtering, CVD, or some other deposition process) and/or on a coating or layer formed on one or more surfaces of the flexible substrate 330.

The electronics 350 disposed on the flexible substrate 330 could include a variety of devices. For example, the electronics 350 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 330. Further, antennas, electrodes, capacitors, resistors, or other components could be formed from such traces or other interconnects formed on the surface of the flexible substrate 330. The electronics 350 can include logic elements configured to operate a light sensor 352 to detect an optical property of an analyte-sensitive substance 362 by illuminating/detecting light emitted from the analyte-sensitive substance 362 via an optical fiber 351 (e.g., to detect a property of the analyte), an antenna (e.g., a loop, dipole, or other type of antenna formed on the flexible substrate 330, or a chip antenna disposed on the flexible substrate 330) to wirelessly indicate information (e.g., concentration levels) about the detected analyte, and/or to provide other functions. Electrical interconnects (e.g., traces), antennas, and/or conductive electrodes (e.g., for an electrochemical analyte sensor, etc.) can be formed from conductive materials patterned on the flexible substrate 330 by a process for precisely patterning such materials, such as deposition, lithography, etc. The conductive materials patterned on the flexible substrate 330 can be, for example, gold, platinum, palladium, titanium, carbon, aluminum, copper, silver, silver-chloride, conductors formed from noble materials, metals, combinations of these, etc.

The body-mountable sensing platform 300 further includes a sensor probe 360 that is attached to the flexible substrate 330. The sensor probe 360 is an elongate element of the body-mountable sensing platform 300 that is configured to penetrate a skin surface and includes an optical fiber 351 such that an analyte-sensitive substance 362 located at a distal end of the optical fiber 351 is in contact with a fluid (e.g., interstitial fluid or blood) containing an analyte of interest (e.g., glucose) when the sensor probe 360 is penetrating the skin. That is, the sensor probe 360 is configured to extend beneath the skin surface into an epidermal, dermal, or subcutaneous tissue of a body that includes the skin surface. The sensor probe 360 could be composed of a flexible material (e.g., polyimide, one or more flexible optically clear polymers formed, e.g., as the optical fiber 351) or a relatively inflexible material; further, a thickness, width, shape, or other properties of the sensor probe 360 could be specified to provide a degree of flexibility or inflexibility.

In some examples, the sensor probe 360 could be partially formed from the same material as the flexible substrate 330; i.e., the sensor probe 360 could include an elongate portion of the flexible substrate 330 that extends from a portion of the flexible substrate 330 that is configured to be mounted to a skin surface and/or on which electronics 350 or other components are disposed. Alternatively, the sensor probe 360 (e.g., the optical fiber 351 of the sensor probe 360) could be attached to the flexible substrate 330. For example, the sensor probe 360 could include the optical fiber 351, wire(s), elongate pieces of shaped silicon, patterned conductive traces, or other elements adhered, welded, bonded, or otherwise attached to the flexible substrate 330. In some examples, the sensor probe 360 could substantially consist of the optical fiber 351. For example, the sensor probe 360 could consist substantially of the optical fiber 351 having disposed on a distal end thereof the analyte-sensitive substance 362 and adhered to the flexible substrate via a proximal end of the optical fiber 351 (e.g., using an optically clear adhesive to optically couple the proximal end of the optical fiber 351 to a light detector and/or light emitter of the light sensor 352). Such sensor probes (i.e., sensor probes including an optical fiber and an analyte-sensitive substance as described herein disposed on a distal end of the optical fiber) could be used for other applications and/or in combination with components or devices other than a flexible substrate (e.g., 330) as described herein.

The substrate 330 includes one or more surfaces suitable for mounting the electronics 350 (including a light sensor 352, a memory 354, and a communication circuit 356), the power supply 340, and the antenna 370. The flexible substrate 330 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. For example, the antenna 370 can be formed by depositing a pattern of gold or another conductive material on the flexible substrate 330. Similarly, interconnects 341, 357 between the electronics 350 and the power supply 340 and between the communication circuit 356 and the antenna 370, respectively, can be formed by depositing suitable patterns of conductive materials on the substrate 330. A combination of microfabrication techniques including, without limitation, the use of photoresists, masks, deposition techniques and/or plating techniques can be employed to pattern materials on the substrate 330. The substrate 330 can be a material, such as polyimide, polyethylene terephthalate ("PET"), parylene, or another material sufficient to structurally support the circuitry and/or electronics.

The power supply 340 is configured to provide energy to power the electronics 350. For example, the power supply 340 could include a battery. Such a battery could be flexible, e.g., the battery could be a flexible lithium-ion battery or some other type of flexible battery. The battery could be flexible to allow the flexible substrate 330 to which the battery is mounted to flex in response to deformation and/or motion of a skin surface to which the flexible substrate 330 is mounted. Such flexibility could be provided to increase the comfort of a living body to which the sensing platform 300 is mounted and/or to minimally interfere with motions and/or activities of such a living body. A battery (or combination of batteries provided as part of the power supply 340) could have a capacity sufficient to power the device for a protracted period of time, e.g., 18 hours, a week, or some other protracted period of time of periodic operation of the light sensor 352, antenna 370, and memory 354 to detect an analyte, to record information related to the analyte in the memory 354, and to wirelessly communicate such detected information to the external reader 380. For example, the battery could be a flexible battery with a capacity of more than approximately 60 microamp-hours and a thickness of less than approximately 0.5 millimeters.

In some examples, the power supply 340 could include a rechargeable battery and could further include some means for recharging such a battery. For example, the power supply 340 could include contacts disposed on a surface of the flexible substrate 330 and configured to receive electrical power from complimentary contacts of a charging device (e.g., the external reader 380). In another example, the sensing platform 300 could include a loop antenna (e.g., a loop antenna comprising conductive traces patterned on the flexible substrate 330) and the power supply 340 could be configured to use the loop antenna to receive RF energy from an external device (e.g., the external reader 380); in some examples, such an RF-energy-receiving antenna could be the same antenna as the antenna 370 used to communicate with external devices.

The user interface 355 is configured to receive inputs from a user (e.g., a user to whose body the device is mounted) and/or present outputs to the user to provide some application(s) of the sensing platform 300. Such user-interface elements (e.g., displays, sensors, buttons) could be flexible and/or mounted to the flexible substrate 330 of the sensing platform 300. In some examples, the user interface 355 could provide means for changing or setting an operational state of the sensing platform 300 and/or for causing the performance of some function by the sensing platform 300. For example, the user interface 355 could provide means for a user to cause the sensing platform 300 to perform a measurement of the physiological property using the light sensor 352 to detect a related optical property of the analyte-sensitive substance 362, to set the sensing platform 300 into a sleep or other low-power state, to set a rate of operation of the light sensor 352 to detect the optical property of the analyte-sensitive substance 362, or to control some other aspect of operation or function of the sensing platform 300. In some examples, the user interface 355 could provide means for inputting calibration or other data to the sensing platform 300, e.g., for inputting calibration data related to the operation of the light sensor 352 and analyte-sensitive substance 362 to detect the physiological property. Additionally or alternatively, the user interface 355 could provide means for inputting information about the state of a user of the sensing platform 300, e.g., to indicate a physical or mental state of the user, to indicate an activity of the user, to indicate that the user has eaten a meal or taken a drug, or to indicate some other information. The user interface 355 could provide means for indicating information to a user, for example, information about the operation of the sensing platform 355 (e.g., battery charge state, an amount of free memory), detected physiological properties (e.g., a blood glucose level detected using the light sensor 352 and analyte-sensitive substance 362), or some other information available to the sensing platform 300.

The user interface 355 could be configured to detect a variety of inputs. The user interface 355 could be configured to detect sound (e.g., voice commands), motions of the sensing platform 300 (e.g., a gesture that includes motion of the skin surface to which the sensing platform is mounts), contact between the sensing platform 300 and a finger or other portion of a user's body, or some other inputs. For example, the user interface 355 could be configured to detect a location, motion, pressure, gesture, or other information about objects (e.g., a finger or other body part) near the sensing platform 300. The user interface 355 could include a capacitive touch sensor configured to detect a single touch, multiple touches, gestures, swipes, or other inputs.

The user interface 355 could be configured to provide a variety of different types of information using a variety of means. The user interface 355 could indicate information related to the operational state of the sensing platform 300 (e.g., to indicate a battery charge state or free memory space of the device) and/or related to the physiological property detected using the light sensor 352 and analyte-sensitive substance 362 (e.g., to indicate a blood glucose level detected using the light sensor 352 and analyte-sensitive substance 362). The user interface 355 could be used to indicate a course of action that a user could take (e.g., to administer a drug, to seek medical assistance). The user interface 355 could be used to indicate some alert generated by the sensing platform 300 (e.g., an alert that a measured physiological property is outside of specified limits, an alert that a user is experiencing an adverse health state). The user interface 355 could include light-emitting elements (e.g., LEDs, OLEDs, displays), color-changing elements (e.g., e-ink elements or displays, LCDs), haptic elements (e.g., vibrators, buzzers, electrohaptic elements), acoustical elements (e.g., buzzers, speakers), or some other elements configured to indicate some information, e.g., to a user. The user interface 355 could include flexible elements, e.g., the user interface 355 could include a flexible OLED display.

The analyte-sensitive substance 362 could take a variety of forms according to the methods used to detect an analyte in fluid (e.g., interstitial fluid) to which the analyte-sensitive substance 362 is exposed. The analyte-sensitive substance 362 can include an analyte-sensitive substance that selectively interacts with the analyte in the fluid and that has an optical property related to the analyte in the fluid. The analyte-sensitive substance 362 can include proteins, enzymes, reagents, ionophores, antibodies, fluorophores, nano-structured surfaces and/or structures, or other substances that selectively bind to, react with, change one or more optical properties in response to the presence of, or otherwise selectively interact with the analyte. The analyte-sensitive substance 362 and light sensor 352 can then detect the selective interaction between the analyte and the analyte-sensitive substance 362 to detect a presence, concentration, or other properties of the analyte.

The optical fiber 351 is configured to transmit light between the analyte-sensitive substance 362 and the light sensor 352. The light sensor 352 is configured to detect the optical property of the analyte-sensitive substance 362 that is related to the analyte. As such, the light sensor 352 could include a light emitter and/or light detector disposed at a proximal end of the optical fiber, such that the light emitter and light detector respectively illuminate and receive light from the analyte-sensitive substance 362 via the optical fiber 351. Other configurations of an analyte sensor are anticipated (e.g., capillary tubes, microfluidic elements, etc. configured to transport interstitial or other fluids of interest along the sensor probe 360 to an analyte-sensitive substance disposed on the flexible substrate 330).

In some examples, the analyte-sensitive substance 362 includes a fluorophore having a fluorescence intensity, a fluorescence lifetime, an emission wavelength, an excitation wavelength, or some other property that is related to the analyte. In some examples, such an analyte-sensitive substance could include a protein or other element configured to selectively bind to the analyte and to experience a conformation change in response to such binding. A fluorophore and a quencher could be attached to the protein such that the distance between the fluorophore and the quencher is related to whether the protein is bound to the analyte; as a result, the degree of fluorescence of the fluorophore could be related to whether the protein is bound to the analyte. Additionally or alternatively, a color, saturation, absorption spectrum, or some other optical property of the analyte-sensitive substance 362 disposed at the end of the sensor probe 360 could be related to the presence, concentration, or some other property of the analyte.

The light sensor 352 could be configured to detect a variety of optical properties of the analyte-sensitive substance 362, via the optical fiber 351, in a variety of ways. In some examples, this could include illuminating the analyte-sensitive substance 362 and detecting a property (e.g., an intensity, a timing) of light responsively emitted from (e.g., reflected by, scattered by, fluorescently emitted by) the analyte-sensitive substance 362. Additionally or alternatively, light emitted from the analyte-sensitive substance 362 due to ambient illumination, chemiluminescence, or other factors or processes could be detected and use do the detect the optical property of the analyte-sensitive substance 362. A light detector of the light sensor 352 could include one or more photodiodes, phototransistors, active pixel sensors, charge-coupled devices, or some other light-sensitive element(s). Further, such a light detector could include wavelength-selective filters, lenses, mirrors, polarization filters, or other optical elements. A light emitter of the light sensor 352 could include one or more LEDs, lasers, or other light-producing elements. Further, such a light emitter could include lenses, mirrors, wavelength- or polarization-selective filters, volume holographic gratings, or other optical elements. In a particular example, the analyte-sensitive substance 362 includes a fluorophore having a fluorescence property (e.g., a fluorescence intensity, a fluorescence lifetime) related to the analyte. In such an example, a light emitter of the light sensor 352 could be configured to emit light at an excitation wavelength of the fluorophore and a light detector of the light sensor 352 could be configured to detect an intensity or other property of light at an emission wavelength of the fluorophore.

In some examples, a light emitter and/or light detector configured to illuminate and/or detect light emitted from the analyte-sensitive substance 362 could be disposed proximate the analyte-sensitive substance 362 (i.e., disposed on the sensor probe 360) and connected to the electronics 350 via conductive interconnects (e.g., metallic interconnects that include traces patterned or otherwise disposed on the sensor probe 360, e.g., on a flexible substrate of the sensor probe 360 to which the optical fiber 351 is mounted).

Optical detection of an analyte can include detecting the interaction between the analyte and the analyte-sensitive substance directly (e.g., by detecting a change in an optical property of the analyte-sensitive substance 362 in response to interaction with the analyte) or indirectly (e.g., by detecting a reaction product of the selective reaction of the analyte, e.g., by detecting hydrogen peroxide produced by oxidation of the analyte by elements of the analyte-sensitive substance 362). For example, the analyte-sensitive substance 362 could include a first substance configured to selectively bind to the analyte such that, when the analyte is bound to the first substance, a local pH is changed. Such an analyte-sensitive substance 362 could further include a second substance having an optical property that is related to the local pH, e.g., a pH-sensitive fluorophore. The optical property of the second substance could be detected (e.g., using a light emitter and/or light detector of the light sensor 352) and used to determine a concentration or other properties of the analyte.

The memory 354 could include a variety of volatile and nonvolatile electronic storage elements configured to provide means for the sensing platform 300 to record and/or log detected information about the analyte (e.g., concentrations measured using the sensor 362 at a plurality of points in time) and/or other information detected by or input to (e.g., via user interface components of the sensing platform 300) the sensing platform 300. For example, the memory 354 could include one or more EEPROM memories, flash memories, NVRAM memories, DRAM memories, SRAM memories, flip-flops, or other information storage elements. The memory 354 could have an information storage capacity sufficient to record some specified period of detected information about the analyte at some specified rate of detection; e.g., the memory 354 could have a capacity sufficient to record more than 18 hours, a week, or some other protracted period of time of detected information (e.g., concentrations) about the analyte when detected at a rate of approximately once per minute. Additionally or alternatively, the sensing platform 300 could be in communication with a memory that is external to the sensing platform 300 and that could be used as described above (e.g., to store analyte measurement data, to store and/or access calibration or other configuration data of the sensing platform 300).

The user interface 355 could include one or more user interface elements configured to receive user input (e.g., from a user whose skin the sensor probe 360 is penetrating and to whose skin surface the flexible substrate 330 is mounted) and/or to indicate information. The body-mountable sensing platform 300 could include lights (e.g., discrete LEDs), displays (e.g., flexible OLED displays), vibration motors, electrohaptic stimulators, or other means for indicating information to a user. Such indicated information could include information about a detected analyte (e.g., a detected concentration of the analyte), information about the status of the body-mountable sensing platform (e.g., battery charge status of the power supply 340, free memory status of the memory 354), alerts (e.g., alerts that a concentration of the analyte is within/outside of a specified range, alerts that a particular health state has been detected, alerts that a user should perform some medical task and/or seek medical attention), or some other information. The body-mountable sensing platform 300 could include buttons, capacitive touch-sensing elements configured to detect touches and/or gestures, temperature sensors configured to detect touches, or other means for detecting input from a user. Such input could include instructions to perform some task (e.g., to operate the light sensor 352 to detect the optical property of the analyte-sensitive substance 362), to change an operational state (e.g., to start and/or stop regular detection of the analyte, to change a frequency at which the analyte is detected), to indicate a personal and/or health state of a user (e.g., to indicate that the user is experiencing nausea, light-headedness, etc.), to indicate that an event has occurred (e.g., that the user has administered/been administered a drug), or some other input/instructions to the body-mountable sensing platform 300.

The electronics 350 include a communication circuit 356 for sending and/or receiving information via the antenna 370. The communication circuit 356 can optionally include one or more oscillators, mixers, frequency injectors, etc. to modulate and/or demodulate information on a carrier frequency to be transmitted and/or received by the antenna 370. In some examples, the body-mountable sensing platform 300 is configured to indicate information (e.g., analyte concentrations detected using the light sensor 352 and analyte-sensitive substance 362) by modulating an impedance of the antenna 370 in a manner that is perceivably by the external reader 380. For example, the communication circuit 356 can cause variations in the amplitude, phase, and/or frequency of backscatter radiation from the antenna 370, and such variations can be detected by the reader 380. Such wireless communication could be compatible with one or more existing backscatter wireless communications standards, e.g., RFID. Additionally or alternatively, the communication circuit 356 and antenna 370 could be configured to transmit wireless signals according to some other method, e.g., according to the BLUETOOTH (e.g., BLUETOOTH Low Energy), ZIGBEE, WIFI, LTE, and/or some other wireless communications standard or scheme. In some examples, such communications (e.g., data transmitted from the sensor platform 300, operational instructions transmitted to the sensor platform 300) could be cryptographically secured; that is, the wireless communications link could be encrypted.

The electronics 350 are connected to the power supply 340 and antenna 370 via interconnects 341, 357. In some examples, the interconnects 341, 357 could include a patterned conductive material (e.g., gold, platinum, palladium, titanium, copper, aluminum, silver, metals, combinations of these, etc.) to connect electrodes, coils, antennas, light emitters, light detectors, or other components of the power supply 340 to terminal(s) on the electronics 350 (e.g., on a controller).

It is noted that the block diagram shown in FIG. 3 is described in connection with functional modules for convenience in description. However, embodiments of the body-mountable sensing platform 300 can be arranged with one or more of the functional modules ("sub-systems") implemented in a single chip, integrated circuit, and/or physical feature or on multiple such elements.

The external reader 380 includes an antenna 388 (or group of more than one antenna) to send and receive wireless signals 371 to and from the body-mountable sensing platform 300. The external reader 380 also includes a computing system with a processor 386 in communication with a memory 382. The external reader 380 can also include one or more of user controls 385, a display 387, and a communication interface 389. The memory 382 is a non-transitory computer-readable medium that can include, without limitation, magnetic disks, optical disks, organic memory, and/or any other volatile (e.g. RAM) or non-volatile (e.g. ROM) storage system readable by the processor 386. The memory 382 can include a data storage 383 to store indications of data, such as sensor readings (e.g., acquired using the light sensor 352), program settings (e.g., to adjust behavior of the body-mountable sensing platform 300 and/or external reader 380), etc. The memory 382 can also include program instructions 384 for execution by the processor 386 to cause the external reader 380 to perform processes specified by the instructions 384. For example, the program instructions 384 can cause external reader 380 to perform any of the function described herein. For example, program instructions 384 may cause the external reader 380 to provide a user interface that allows for retrieving information communicated from the body-mountable sensing platform 300 (e.g., detected optical property outputs from the light sensor 352 and/or related analyte properties) by displaying that information on the display 387 in response to commands input through the user controls 385. The external reader 380 can also include one or more hardware components for operating the antenna 388 to send and receive the wireless signals 371 to and from the body-mountable sensing platform 300. For example, oscillators, frequency injectors, encoders, decoders, amplifiers, filters, etc. can drive the antenna 388 according to instructions from the processor 386.

The external reader 380 can also be configured to include a communication interface 389 to communicate signals via a communication medium 391 to and from a remote system 390. For example, the remote system 390 may be a smart phone, tablet computer, laptop computer, or personal computer, and communication interface 389 and communication medium 391 may be a BLUETOOTH module and wireless BLUETOOTH communication signals, respectively. In this example, the external reader 380 may be configured to send information about the analyte collected using the light sensor 352 and analyte-sensitive substance 362 to the smart phone, tablet computer, laptop computer, or personal computer for storage and offline analysis. In another example, the remote system 390 is a server at a clinic or physician's office, the communication interface 389 is a WIFI radio module, and the communication medium 391 is elements of the internet sufficient to enable the transfer of data between the remote server and the WIFI radio module. A physician may use this data to make determinations or diagnoses related to the subject's condition. Further, the external reader 380 may be configured to receive signals from a remote server, such as instructions sent by a physician at a remote location to, for example, increase or decrease sampling frequency. Communication interface 389 could be configured to enable other forms of wired or wireless communication; for example, CDMA, EVDO, GSM/GPRS, WIMAX, LTE, infrared, ZIGBEE, ETHERNET, USB, FIREWIRE, a wired serial link, or near field communication.

The external reader 380 can be a smart phone, digital assistant, or other portable computing device with wireless connectivity sufficient to provide the wireless communication link 371. The external reader 380 can also be implemented as an antenna module that can be plugged in to a portable computing device, such as in an example where the communication link 371 operates at carrier frequencies not commonly employed in portable computing devices. In some instances, the external reader 380 is a special-purpose device configured to be periodically placed relatively near the sensing platform 300 to allow the wireless communication link 371 to operate with a low power budget.

In some examples, the light sensor 352 and analyte-sensitive substance 362 could be configured to detect glucose in the body of a person and the external reader 380 could include or be in contact with an insulin pump. Such an insulin pump could include a supply of insulin and a pump configured to provide the insulin, at a controlled rate, into the body of the person (e.g., through a tube placed in and/or through the skin of the body of the person using, e.g., a needle). In such examples, the insulin pump could be operated based on measurements of glucose levels (e.g., concentrations) in the body of the person detected using the light sensor 352 and analyte-sensitive substance 362. For example, the insulin pump could be operated to provide insulin at a rate based on the detected glucose levels such that the blood glucose levels of the person are maintained within a specified range, or according to some other scheme (e.g., the insulin pump could be operated as part of a feedback loop that includes the light sensor 352). Additionally or alternatively, the external reader 380 could include or be in contact with a pump for some other pharmaceutical and could be operated to provide that pharmaceutical at a controlled rate based on a detected level of glucose or of some other analyte detected using the light sensor 352 and analyte-sensitive substance 362.

In an example where the body-mountable sensing platform 300 has been mounted to skin of a living body such that the analyte-sensitive substance 362 is in contact with interstitial fluid of the living body, the sensing platform 300 can be operated to detect the analyte (e.g., to measure a concentration of the analyte) in the interstitial fluid. The interstitial fluid is an extravascular fluid that suffuses many of the tissues of a living animal body. The interstitial fluid is continuously replenished by the blood supply through capillaries in the structure of tissue (e.g., dermal tissue, subcutaneous tissue) and includes many biomarkers found in blood that are analyzed to characterize a person's health condition(s). For example, the interstitial fluid includes urea, glucose, calcium, sodium, cholesterol, potassium, phosphate, other biomarkers, etc. The biomarker concentrations in the interstitial can be systematically related to the corresponding concentrations of the biomarkers in the blood, and a relationship between the two concentration levels can be established to map interstitial fluid biomarker concentration values to blood concentration levels. Thus, measuring interstitial fluid analyte concentration levels using sensing platforms as described herein can provide a technique for monitoring analyte levels in comparison to blood sampling techniques performed by lancing a volume of blood to be analyzed outside a person's body. Moreover, the body-mountable sensor platform disclosed here can be operated substantially continuously to enable real time measurement of analyte concentrations or other information about an analyte.

In some embodiments, the body-mountable sensing platform 300 can operate to non-continuously ("intermittently") indicate information related to a detected analyte (e.g., concentration values of the analyte). For example, the body-mountable sensing platform 300 could operate to periodically operate the light sensor 352 to detect an analyte by detecting the related optical property of the analyte-sensitive substance 362 and to store information related to the detection of the analyte in the memory 354. The sensing platform 300 could then less frequently operate to transmit stored information relating to more than one detection of the analyte. Additionally or alternatively, a user could operate the external reader 380 to request such information transmission by the sensing platform 300. In another example, the sensing platform 300 could indicate to a user (e.g., via a light, vibration motor, or other user interface element(s) of the sensing platform) that the user should operate the external reader 380 to receive such transmitted information from the sensing platform (e.g., due to the memory 354 being nearly full, due to a battery of the power supply 340 being nearly depleted). Other operations of the systems shown to continuously, periodically, and/or intermittently use the light sensor 352 and analyte-sensitive substance 362 to detect an analyte, use the memory 354 to store information related to the detected analyte, and/or use the antenna 370 to wirelessly indication such information are anticipated.

IV. EXAMPLE BIOSENSORS

Sensors configured to detect the presence, concentration, or some other property of an analyte of interest could be configured in a variety of ways and incorporated into a variety of different systems of devices. For example, a sensor or analyte-sensitive elements thereof could be included on a distal end of a sensor probe that is configured to penetrate skin of a living body, such that the sensor can detect the analyte in interstitial (or other fluid) within the skin when the sensor probe penetrates the skin. Further, such sensor probes could be included as part of a body-mountable sensing platform that includes a flexible substrate, to which the sensor probe is attached, and that is configured to be mounted (e.g., by an adhesive layer or some other means) to a skin surface. A sensor could detect the analyte electro-chemically (e.g., by detecting a voltage between and/or a current passing through two or more electrodes), optically (by detecting an optical property of the analyte and/or some other element(s) of the environment and/or of the sensor), or by some other means.

A sensor can be configured to detect an analyte by including one or more substances that selectively interact with the analyte. Such substances could have an electrical, optical, or other property that is related to the presence, concentration, or other property of the analyte. Additionally or alternatively, an analyte-sensitive substance could selectively react with and/or selectively catalyze a reaction of the analyte and products of such a reaction could be detected by a sensor to allow for detection of the analyte. Analyte-sensitive substances can coat one or more surfaces of a sensor (e.g., a distal end of an optical fiber configured to optically couple an analyte-sensitive substance to a light detector, light emitter, or other elements of a light sensor), can be incorporated into an analyte-permeable layer of polymer, gel, or some other material, or can be localized and/or incorporated on or into a sensor by some other method.

In some examples, a sensing platform can include an analyte-sensitive substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of a substance disposed at the end of the sensor probe could be related to the presence, concentration, or some other property of the analyte. In a particular example, the analyte-sensitive substance could include a fluorophore that includes a boronic acid moiety such that binding of glucose to the boronic acid moiety causes a conformational change or other effect on the fluorophore such that a fluorescence property of the fluorophore is changed (e.g., such that binding of glucose to the boronic moiety quenches a fluorescent excitation state of the fluorophore).

In some examples, a first component of the analyte-sensitive substance could be configured to selectively cause a chemical reaction of the analyte (e.g., the first component could include an enzyme, catalyst, or other analyte-selective agent), and one or more reaction products of the reaction could be optically detected, e.g., by detecting an optical property of a second component of the analyte-sensitive substance (e.g., a pH-sensitive fluorophore). For example, the first component of the analyte-sensitive substance could include an agent that selectively oxidizes and/or reduces the analyte (e.g., the analyte-sensitive substance could be an oxidoreductase enzyme or protein). For example, the analyte could be glucose, pyruvate, or urea and the analyte-selectively substance could be glucose oxidase, pyruvate oxidase, or urease, respectively. Such a reaction could produce reaction products including oxides (e.g., hydrogen peroxide) and the second component of the analyte-sensitive substance could include an oxide-sensitive fluorophore (e.g., a fluorophore having an fluorescent excitation state that is quenched by an oxide produced by the reaction of the analyte by the first component).

The sensor and/or a sensor platform including the sensor could include a light emitter and/or a light detector configured to illuminate and/or to receive light emitted from the analyte-sensitive substance, respectively, in order to determine the optical property of the substance that is related to the analyte. In some examples, the light emitter and/or light sensor could be disposed proximate to the analyte-sensitive substance (e.g., the analyte-sensitive substance could be disposed on a surface of a light detector). Additionally or alternatively, one or both of the light emitter and light detector could be optically coupled to the analyte sensitive substance using one or more optical fibers, lenses, mirrors, diffraction gratings, optical waveguides, or other optical elements. For example, the analyte-sensitive substance (e.g., a hydrogel or other analyte-permeable polymer within which fluorophores, enzymes, proteins, or other elements having an optical property related to the analyte) could be disposed at a distal end of an optical fiber and the light emitter and/or light detector could be disposed at a proximal end of the optical fiber such that light emitted by the light source is transmitted to the analyte-sensitive substance and/or such that light emitted from the analyte-sensitive substance is transmitted to the light detector.

FIG. 4A shows a sensor probe 400 that includes an optical fiber 410. The optical fiber has a distal end 420 on which an analyte-sensitive substance 425 is disposed. The distal end 420 is configured to contact a fluid (e.g., interstitial fluid) and the analyte-sensitive substance 425 is configured to have an optical property (e.g., a fluorescence, a fluorescence lifetime, a color, an absorption spectrum) that is related to the presence, concentration, or other property of the analyte in the fluid to which the analyte-sensitive substance 425 is exposed. A light emitter 430 (e.g., an LED, a laser, etc.) and a light detector 440 (e.g., a photodiode, a phototransistor, a photoresistor, etc.) are disposed at a proximal end 421 of the optical fiber 410. The optical fiber 410 is configured (e.g., is composed of a material that is optically transparent across one or more ranges of wavelengths of light) such that the light emitter 430 can emit illumination 435 to illuminate the analyte-sensitive substance 425 via the optical fiber 410. Further, the light detector 440 can detect responsively emitted light 445 that is emitted from the analyte-sensitive substance 425 via the optical fiber 410.

Note that the sensor 400 could include elements additional to those shown. In some examples, the analyte-sensitive substance 425 could be disposed in and/or include a layer of polymer, gel, or other analyte-permeable material disposed at the distal end 420 of the optical fiber 410. Additionally or alternatively, a protective layer could be disposed over the analyte-sensitive substance 425. In some examples, the optical fiber 410 could be disposed on (e.g., adhered to, formed on) a flexible substrate that is, in turn, continuous with a flexible substrate that is configured to be mounted to a skin surface and on which electronics (including, e.g., the light emitter 430 and light detector 440) could be disposed. Further, one or both of the light emitter 430 and light detector 440 could be disposed proximate the analyte-sensitive substance 425 such that the light emitter 430 and/or light detector 440 could illuminate and/or receive emitted light from, respectively, the analyte-sensitive substance 425 directly rather than through an optical fiber (e.g., 410). In such examples, the light emitter 430, light detector 440, and/or analyte-sensitive substance 425 could be disposed on the distal end of a sensor probe as described in connection with other embodiments described herein (e.g., embodiments described in relation to FIGS. 1A, 1B, and 2A-2D).

FIG. 4B shows the optical fiber 410 in cross-section. The optical fiber 410 includes a core 415 composed of a material having a first refractive index and a cladding layer 417 disposed on the outside of the core 415 and composed of a material having a second refractive index that is lower than the first refractive index. As a result, a portion of the light entering a first end of the optical fiber 410 (e.g., a portion of light emitted from the analyte-sensitive substance 425 that enters the distal end 420 of the optical fiber 410) can experience total internal reflection against the interface between the core 415 and the cladding layer 417 such that a substantial amount of the light that enters the first end of the optical 410 exits the optical fiber 410 via a second end of the optical fiber (e.g., to exit the proximal end 421 of the optical fiber 410 to be detected by the light detector 440). The core 415 and/or cladding layer 417 could be composed of glasses, polymers, or other optical transparent materials. Note that the illustrated optical fiber 410 is intended as a non-limiting example; differently configured optical fibers (e.g., optical fibers having additional layers, having non-circular geometries, having refractive index gradients, or otherwise configured) are anticipated that could be used, as described herein, to transmit light between an analyte-sensitive substance (e.g., an analyte-sensitive substance disposed on a sensor probe configured to penetrate skin) and light emitters and/or light detectors configured to detect an optical property of the analyte-sensitive substance.

Note that the disposition of an analyte-sensitive substance as and/or within a volume of material disposed at a distal end of an optical fiber (e.g., analyte-sensitive substance 425 disposed at the distal end 420 of the optical fiber 410) as illustrated in FIG. 4A is intended as a non-limiting example embodiment. Analyte-sensitive substances could be disposed as layers (e.g., cross-linked layers of proteins or other substances) on one or more surfaces of an optical fiber, disposed within an optical fiber (e.g., within the cladding layer or other layers of an optical fiber), and/or disposed as part of materials of an optical fiber (e.g., diffused within or otherwise disposed throughout a polymer or other material that comprises a core, cladding layer, or other element(s) of an optical fiber).

As an example, FIG. 5A shows a sensor probe 500*a* that includes an optical fiber 510*a*. The optical fiber includes a core 515*a* surrounded by a cladding layer 517*a*. The optical fiber has a distal end 520*a* at which an analyte-sensitive substance 525*a* is disposed. Specifically, the analyte-sensitive substance 525*a* is disposed within the cladding layer 517*a* at the distal end 520*a*. This could include the region within the cladding layer 517*a* at the distal end 520*a* of the optical fiber 510*a* being filled with or otherwise having disposed within a polymer or other analyte-permeable material that includes the analyte-sensitive substance 525*a*. Additionally or alternatively, the core 515*a* could be composed of a material that is permeable to the analyte, and the distal end of the core 515*a* could include an analyte-sensitive substance (e.g., a protein, fluorophore, or other elements of the analyte-sensitive substance 525*a* could be diffused within, attached within or to a polymer network of, or otherwise disposed within the material of the core 515*a*). That is, the illustrated analyte-sensitive substance 525*a* could form part of the core 515*a*. The distal end 520*a* is configured to contact a fluid (e.g., interstitial fluid) and the analyte-sensitive substance 525*a* is configured to have an optical property (e.g., a fluorescence, a fluorescence lifetime, a color, an absorption spectrum) that is related to the presence, concentration, or other property of the analyte in the fluid to which the analyte-sensitive substance 525*a* is exposed.

A light emitter (e.g., an LED, a laser, etc.; not shown) and a light detector (e.g., a photodiode, a phototransistor, a photoresistor, etc.; not shown) can be disposed at a proximal end of the optical fiber 510*a*. The optical fiber 510*a* is configured (e.g., is composed of a material that is optically transparent across one or more ranges of wavelengths of light) such that such a light emitter can emit illumination to illuminate the analyte-sensitive substance 525*a* via the optical fiber 510*a*. Further, such a light detector can detect responsively emitted light that is emitted from the analyte-sensitive substance 525*a* via the optical fiber 510*a*.

As another example, FIG. 5B shows a sensor probe 500*b* that includes an optical fiber 510*b*. The optical fiber includes a core 515*b* surrounded by a cladding layer 517*b*. The optical fiber has a distal end 520*b* at which an analyte-sensitive substance 525*b* is disposed. Specifically, the analyte-sensitive substance 525*b* is disposed as a thin layer on the distal end 520*a*. This could include a protein, fluorophore, or other elements of the analyte-sensitive substance 525*b* being crosslinked into a layer adhered to the distal end 520*b* of the optical fiber 510*b*. Additionally or alternatively, the illustrated analyte-sensitive substance 525*b* could be a polymer layer or layer of other analyte-permeable material and proteins, fluorophores, or other analyte-sensitive elements of the analyte-sensitive material 525*b* could be diffused within, attached within or to a polymer network of, or otherwise disposed within such a polymer layer or layer of other analyte-permeable material.

A light emitter (e.g., an LED, a laser, etc.; not shown) and a light detector (e.g., a photodiode, a phototransistor, a photoresistor, etc.; not shown) can be disposed at a proximal end of the optical fiber 510*b*. The optical fiber 510*b* is configured (e.g., is composed of a material that is optically transparent across one or more ranges of wavelengths of light) such that such a light emitter can emit illumination to illuminate the analyte-sensitive substance 525*b* via the optical fiber 510*b*. Further, such a light detector can detect responsively emitted light that is emitted from the analyte-sensitive substance 525*b* via the optical fiber 510*b*.

As described herein, an analyte-sensitive substance can be disposed within a polymer layer or volume formed on or within a distal end of an optical fiber. Such a polymer can be permeable to the analyte and contain a reagent that selectively interacts with the analyte to change an optical property of the analyte-sensitive substance (e.g., to change a fluorescence intensity of a fluorophore) that can be sensed by light sensor (e.g., a light detector and/or light emitter) and/or by some other element. In some examples, such a polymer material is a hydrogel that includes 2-hydroxyethyl methacrylate units. Such a hydrogel could contain additional polymer units or other chemicals to adjust a permeability of the hydrogel to the analyte, to bind a protein, enzyme, fluorophore, or other analyte-sensitive element(s) of the analyte-sensitive substance within the hydrogel, to increase a degree of crosslinking of the hydrogel, or to specify one or more other properties of the hydrogel. For example, such a hydrogel could additionally include di(ethylene glycol) dimethacrylate units.

The polymer material could be formed on a surface of a sensing platform (e.g., on a distal surface of an optical fiber) by forming a solution containing monomer units (e.g., units of 2-hydroxyethyl methacrylate), crosslinker units (e.g., units of di(ethylene glycol) dimethacrylate), copolymer units, the analyte-sensitive substance, and/or a polymerization initiator (e.g., the photoinitiator 2,2-dimethoxy-2-phenylacetophenone), depositing the formed solution on the surface of the sensing platform (e.g., on a distal end of an optical fiber), and polymerizing the solution into a polymer material containing the analyte-sensitive substance. In some examples, light used to polymerize the deposited solution could be supplied through the optical fiber, e.g., the solution could be disposed on a distal end of the optical fiber and light could be supplied to polymerize the deposited solution by being transmitted via the optical fiber (e.g., provided via a proximal end of the optical fiber). In such examples, the solution could be deposited proximate the distal end of the optical fiber by submerging or otherwise dipping the distal end of the optical fiber in a reservoir of the solution. The optical fiber could then be removed from the reservoir and the deposited solution could be polymerized. Alternatively, light could be provided, via the optical fiber, to polymerize the solution of the reservoir that is proximate the distal end of the optical fiber.

The optical sensors as described herein can additionally include protective layers disposed over elements of the optical sensors, e.g., over an analyte-sensitive substance of such optical sensors. Such protective layers could be composed of a polymer, gel, or other material that is permeable to the analyte. In some examples, a permeability, thickness, or other properties of such a protective layer could be specified to control a rate of diffusion of the analyte from interstitial fluid to the analyte-sensitive substance (e.g., a polymer layer containing the analyte-sensitive substance). In some examples, the protective layer could be a hydrogel, e.g., a hydrogel that includes units of 2-hydroxethyl methacrylate and/or units of di(ethylene glycol) dimethacrylate. Additionally or alternatively, the protective layer could include one or more polymers, including polydimethylsiloxane, polyvinylchloride, polyethylene terephthalate, polymethyl methacrylate, silicone hydrogels, or combinations of these or other polymers.

Such a protective layer could be formed by a variety of processes, including CVD, application of a monomer solution followed by polymerization, precipitation of elements of the protective layer from a solution into which an optical fiber or other elements of n optical sensor have been dipped, or some other methods. For example, the optical sensor (and/or some terminal aspect thereof, e.g., a specified length of the distal end of optical fiber) could be dipped in a solution containing a monomer, co-monomer, crosslinker, and/or other chemicals (e.g., units of 2-hydroxethyl methacrylate and/or units of di(ethylene glycol) dimethacrylate), and the solution applied to the optical sensor could then be polymerized to form the protective layer. In some examples, such a deposited solution could be polymerized by exposing the solution to light (e.g., to ultraviolet light having a wavelength specified to activate a photo-initiator in the deposited solution).

An optical fiber of a sensing platform as described herein (e.g., 352, 410, 510a, 510b) could be disposed on an elongate substrate, e.g., to provide mechanical support or rigidity, to attach the optical fiber to some other element(s) of the sensing platform (e.g., a flexible substrate that is configured to be mounted to a skin surface), to provide the ability to pierce skin with the optical fiber and attached elements, or according to some other application(s). Such an elongate substrate could include a flexible material, a rigid material, or a combination of flexible and rigid materials. For example, the elongate substrate could include polyimide. The elongate substrate could be configured to penetrate and/or pierce skin (e.g., by being sufficiently rigid and/or sharpened). Additionally or alternatively, the elongate substrate could be configured to penetrate skin in combination with some other elements (e.g., in combination with a half-needle to which the elongate substrate is coupled) and/or to penetrate an existing puncture, cut, or other incision into skin (provided, e.g., by a needle, lancet, scalpel, or other device). The elongate substrate could be composed of a material on which conductive traces can be formed (e.g., by sputtering, CVD, photoresistive processes, or some other methods) and/or could be coated with a material such that conductive traces can be formed on the elongate substrate.

A sensor probe or other element of a sensing platform that is configured to penetrate skin (or other tissues or materials of an environment on interest) could include one or more optical fibers and associated optical substances (e.g., analyte-sensitive substances having optical properties related to an analyte), as described herein. In some examples, such multiple optical fibers and optical substances could be provided to detect multiple different analytes (e.g., by including multiple different optical substances having respective optical properties related to respective different analytes), to detect an analyte at multiple different locations of depths within an environment (e.g., by the multiple different optical fibers having respective different lengths), or to provide some other functionality. In some examples, multiple optical fibers and respective multiple optical substances could provide for higher-accuracy, lower noise, or otherwise improved detection of an analyte.

This could include detecting optical properties of first and second optical substances having respective different sensitivities to the analyte. For example, the first optical substance could include a fluorophore to which a boronic acid moiety is attached. Such a fluorophore could have a fluorescence intensity or other optical property that is related to a concentration of glucose in a fluid to which the first optical substance is exposed. The second optical substance could include substantially the same fluorophore as the first optical substance, but lacking the boronic acid moiety such that the second optical substance has a fluorescence intensity or other optical property that is less strongly affected by the analyte in a fluid to which the second optical substance is exposed. The first and second optical substances could be disposed at the distal ends of respective first and second optical fibers such that the optical properties of the first and second optical fibers can be detected optically (e.g., by illuminating and/or detecting light emitted from the optical substances via respective optical fibers).

In such examples, an optical property of the second optical substance could be used as an offset or used otherwise to determine a concentration or other property of the analyte in fluid to which the optical substances are exposed. For example, a detected optical property of the second optical substance could be related to a pH, osmolarity, or other property of the fluid to which the optical substances are exposed, an autofluorescence of tissue proximate the optical substances, an ambient light in the environment of the optical substances, or some other properties of the environment of the optical substances. A detected optical property of the first optical substance could be related to such environmental properties and further related to the analyte in the fluid (e.g., more affected by the analyte than the optical property of the second optical substance). Thus, the detected optical properties of the first and second optical substances could be used to determine a concentration or other properties of the analyte (e.g., by determining a difference, ratio, or other relationship between the detected optical properties).

Figure 6:
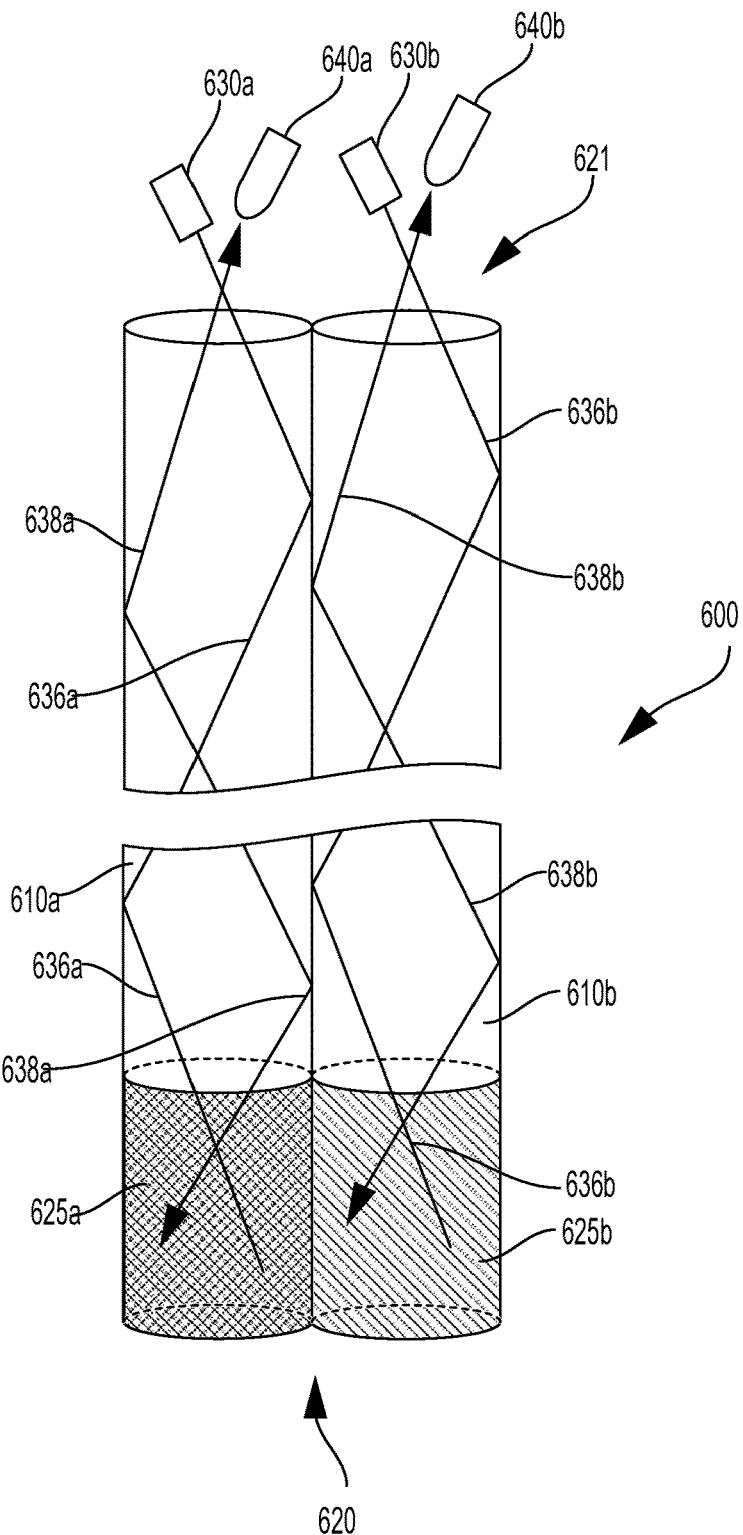
FIG. 6 is an aspect view of an example sensor that includes two optical fibers.

As an example, FIG. 6 shows a sensor probe 600 that includes first 610a and second 610b optical fibers. The sensor probe has a distal end 620 at which an analyte-sensitive substance 625a and an optical substance 625b are disposed. The distal end 620 is configured to contact a fluid (e.g., interstitial fluid) and the analyte-sensitive substance 625a is configured to have an optical property (e.g., a fluorescence, a fluorescence lifetime, a color, an absorption spectrum) that is related to the presence, concentration, or other property of the analyte in the fluid to which the analyte-sensitive substance 625a is exposed. The optical substance 625b is configured to have a corresponding optical property that is less related to the presence, concentration, or other property of the analyte than the analyte-sensitive substance 625a. In some examples, this could include the optical property of the optical substance 625b being substantially unrelated to the analyte in the fluid to which the optical substance 625b is exposed.

First 630a and second 630b light emitters (e.g., LEDs, lasers, etc.) and first 640a and second 640b light detectors (e.g., photodiodes, phototransistors, photoresistors, etc.) are disposed at a proximal end 621 of the sensor probe 600. The optical fibers 610a, 610b are configured (e.g., are composed of a material that is optically transparent across one or more ranges of wavelengths of light) such that the light emitters 630a, 630b can emit respective beams of illumination 636a, 636b to illuminate the analyte-sensitive substance 625a and optical substance 625b, respectively, via respective optical fibers 610a, 610b. Further, the light detectors 640a, 640b can detect respective responsively emitted lights 638a, 638b that are emitted from the analyte-sensitive substance 625a and optical substance 625b, respectively, via respective optical fibers 610a, 610b.

Moreover, it is particularly noted that while analyte sensors and body-mountable sensor platforms including such sensors are described herein by way of example as a body-mountable, skin-penetrating and/or skin-surface-mounted devices, it is noted that the disclosed sensors, optical sensor arrangements (e.g., arrangements of optical fibers, light detectors, light emitters, and/or analyte-sensitive substances), and sensing platforms can be applied in other contexts as well. For example, sensors and sensing platforms disclosed herein may be included in body-mountable and/or implantable sensors and/or sensing platforms used to measure an analyte in a fluid of an animal. In another example, sensors and/or sensing platforms disclosed herein may be included in devices to measure an analyte in an environmental fluid, such as a fluid in a river, lake, marsh, reservoir, water supply, sanitary sewer system, or storm sewer system. In another example, sensors and/or sensing platforms disclosed herein may be included in devices to measure an analyte in a fluid which is part of a process, such as a waste treatment process, pharmaceutical synthesis process, food preparation process, fermentation process, or medical treatment process

V. EXAMPLE METHODS

Figure 7:
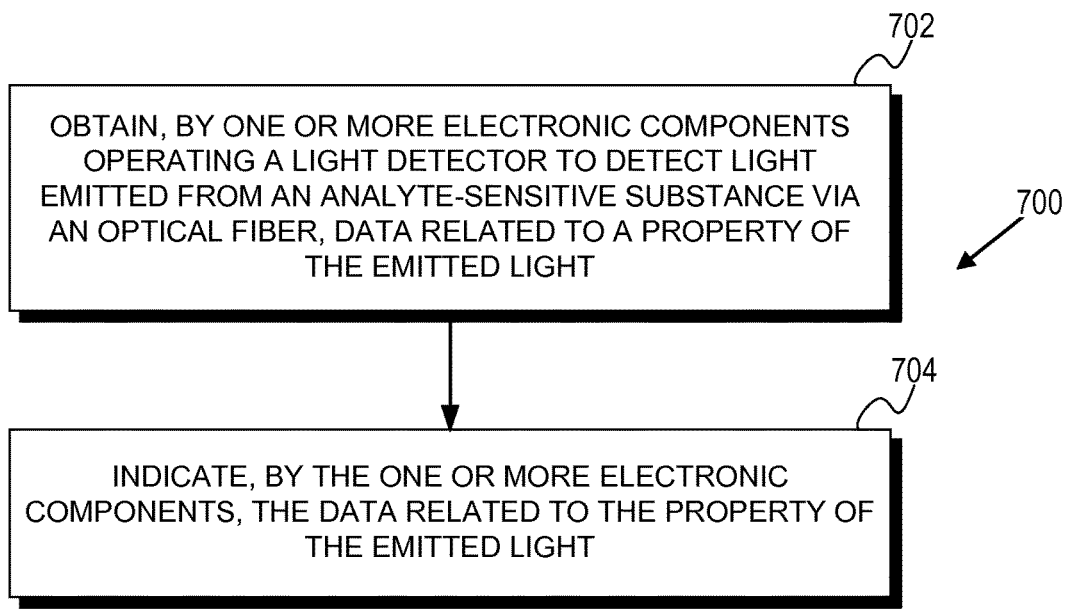
FIG. 7 is a flowchart of an example process for operating a body-mountable device.

FIG. 7 is a flowchart of a method 700 for operating a body-mountable device to measure an analyte in interstitial fluid within skin of a body, e.g., to detect the concentration of the analyte. The body-mountable device includes (i) a flexible substrate configured to be mounted to a skin surface, (ii) a sensor probe that has a first end attached to the flexible substrate and that has a second end that is configured to extend beneath the skin surface to contact interstitial fluid, and that includes an optical fiber that extends from the first end of the sensor probe to the second end of the sensor probe, (iii) an analyte-sensitive substance that is disposed at the second end of the sensor probe and that has an optical property that is affected by an analyte in the interstitial fluid, (iv) a light detector, and (v) one or more electronic components disposed on the substrate.

The method 700 includes obtaining, by one or more of the electronic components operating the light detector to detect light emitted by the analyte-sensitive substance via the optical fiber, data related to a property of the emitted light (702). In some examples, the light emitted from the analyte-sensitive substance could be emitted in response to illumination of the analyte-sensitive substance, and obtaining data related to a property of the emitted light (702) could include operating a light emitter to provide such illumination via the optical fiber. Obtaining data related to a property of the emitted light (702) could include determining an intensity, fluorescence lifetime, color, wavelength, spectral profile, or some other properties of the emitted light and/or optical properties of the analyte-sensitive substance at a plurality of different points in time (e.g., at a specified rate). Obtaining data related to a property of the emitted light (702) could be performed in response to a request for such data (e.g., by an external system in communication with the body-mountable device).

The method 700 additionally includes indicating, by the one or more electronic components, the data related to the property of the emitted light (704). Indicating data related to the property of the emitted light (704) could be performed periodically, in response to a request for such data (e.g., from an external system in communication with the body-mountable device), in response to the determination that an event has occurred and/or a specified condition is satisfied (e.g., in response to a determination by the body-mountable device of a particular health state of a body to which the device is mounted). Indicating data related to the property of the emitted light (704) could be performed securely, e.g., by encrypting information that is indicated over a wireless communications link (e.g., via an RFID link). Indicating data related to the property of the emitted light (704) could include transmitting additional data, e.g., information about the status of the device (e.g., battery charge status, memory free space status), other information gathered by the device (e.g., temperature data obtained using a temperature sensor of the device), user inputs to the device (e.g., taps, swipes, or other inputs to buttons, capacitive sensors, or other elements of the device to control the device, indicate user states or information or according to some other application), or some other information. Indicating data related to the property of the emitted light (704) could include operating a user interface (e.g., an indicator light, a buzzer, a speaker, a display) to indicate the data to a user, e.g., to indicate a concentration of the analyte determined based on the detected property of the emitted light.

The method 700 could include mounting the body-mountable device to the skin surface. Mounting the body-mountable device to the skin surface could include using an adhesive layer of the body-mountable device to mount the flexible substrate to the skin surface. Additionally or alternatively, a liquid adhesive, tape, strap, dry adhesive, or other means could be used to mount the flexible substrate to the skin surface. Further, mounting the body-mountable device to the skin surface could include installing the sensor probe in the skin such that the sensor probe penetrates the skin and further such that the analyte-sensitive substance disposed on the sensor probe is placed in contact with interstitial fluid within the skin. This could include placing the sensor probe in a puncture, cut, or other incision that has already been formed in the skin (e.g., by a needle, a lancet, a scalpel, or by some other means). Alternatively, the sensor probe could be configured to penetrate and/or pierce the skin (e.g., by being sharpened and/or having a sufficiently high rigidity).

The method 700 could include additional steps. For example, the method 700 could include using a memory of the body-mountable device to store information relating to the analyte (e.g., detected analyte concentration values, detected optical properties of the analyte-sensitive substance). The method 700 could include determining a health state, a course of treatment, a dose and/or timing of administration of a drug, or some other information based on detected analyte data and/or detected optical properties. The method 700 could include indicating detected optical properties, determined analyte data, determined dosing and/or timing of administration of a drug, or some other information generated by and/or available to the device using a user interface of the device (e.g., LEDs, displays, vibrators) and/or via a user interface of an external device in communication with the device. Additional and/or alternative steps, or alternative embodiments of the listed steps, are anticipated.

Figure 8:
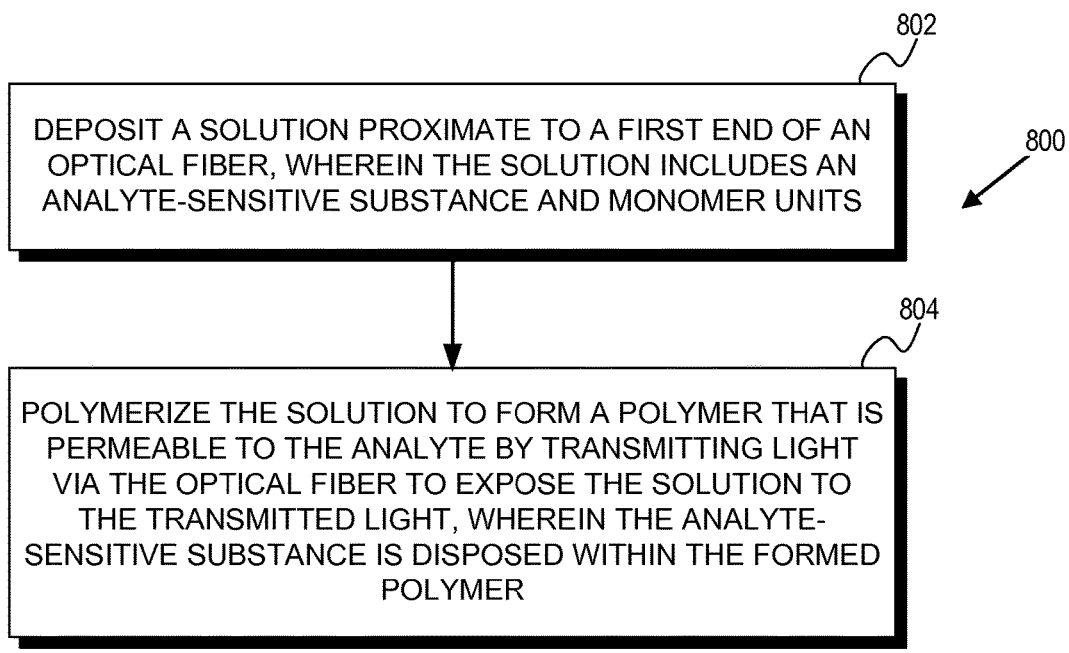
FIG. 8 is a flowchart of an example process for fabricating a sensor.

FIG. 8 is a flowchart of a method 800 for fabricating a sensor (e.g., a sensor that is a part of a body-mountable sensing platform as described elsewhere herein). The method 800 includes depositing a solution proximate to a first end of an optical fiber, wherein the solution includes an analyte-sensitive substance and monomer units (802). The solution could be deposited by dipping the optical fiber in a reservoir of the solution, by spraying, by applying the solution with a brush or other applicator, by chemical vapor deposition, or by some other steps. Depositing the solution on the distal end of the optical fiber (802) could include submerging the distal end of the optical fiber in a reservoir of the solution. The monomer units could include units of a hydrogel or other polymer that is permeable to the analyte. For example, the monomer units could include 2-hydroxyethyl methacrylate units. Such a solution could contain additional polymer units or other chemicals to adjust a permeability of the hydrogel to the analyte, to bind the analyte-sensitive substance or other related substances within the hydrogel, in increase a degree of crosslinking of the hydrogel, or to specify one or more other properties of the hydrogel. For example, such a hydrogel could additionally include di(ethylene glycol) dimethacrylate units.

The method additionally includes polymerizing the solution to form a polymer that is permeable to the analyte by transmitting light via the optical fiber to expose the solution to the transmitted light, wherein the analyte-sensitive substance is disposed within the formed polymer (804). This could include transmitting ultraviolet light via the optical fiber to polymerize the solution on the end of the optical fiber. Polymerizing the polymerizing the solution to form a polymer (804) could include mounting the optical fiber to a light emitter and operating the light emitter to emit light via the optical fiber to polymerize the monomer units in the solution.

The method 800 could include additional steps. The method 800 could include forming a protective layer (e.g., a layer of a protective polymer, a hydrogel, or some other protective material) over all or part of the formed polymer. The method 800 could include mounting the optical fiber to a flexible substrate and forming antennas, interconnects, or other elements on the flexible substrate (e.g., by patterning metal or other conductive material on the flexible substrate). The method 800 could include disposing components on such a flexible substrate. Components such as electronic chips may be disposed on the substrate and connected to the other components by methods familiar to one skilled in the art (e.g., pick-and-place machines, flip-chip mounting). The method 800 could include a calibration step, wherein the formed polymer containing the analyte-sensitive substance is exposed to test fluids having a range of known analyte concentrations. Properties of light emitted from the analyte-sensitive substance (e.g., in response to illuminating of the analyte-sensitive substance) or other information about the analyte measured using the formed analyte-permeable polymer when exposed to respective fluids having known concentrations of the analyte could be used to calibrate an optical sensor formed from the optical fiber and formed polymer. Additional and/or alternative steps, or alternative embodiments of the listed steps, are anticipated.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A body-mountable device comprising:
    a flexible substrate having a first side and a second side opposite the first side, wherein the flexible substrate is comprised by a single piece of material that is configured to be mounted to a skin surface and that is shaped to have an elongate extension having a distal end configured to extend beneath the skin surface to contact interstitial fluid;
    an adhesive layer disposed on the first side of the flexible substrate, wherein the adhesive layer is configured to adhere the flexible substrate to the skin surface;
    an optical fiber disposed on the elongate extension of the flexible substrate, wherein the optical fiber extends along a length of the elongate extension to the distal end of the elongate extension;
    an analyte-sensitive substance, wherein the analyte-sensitive substance is disposed at the distal end of the elongate extension of the flexible substrate, and wherein the analyte-sensitive substance has an optical property affected by an analyte in the interstitial fluid;
    a light detector;

one or more electronic components disposed on the single piece of material of the flexible substrate, wherein the one or more electronic components are configured to (i) operate the light detector to detect, via the optical fiber, a property of light emitted from the analyte-sensitive substance and (ii) indicate data related to the detected property of the emitted light, wherein at least one of the one or more electronic components is disposed on the first side of the flexible substrate; and a conductive trace patterned on a surface of the flexible substrate, wherein at least one of the one or more electronic components is connected to the flexible substrate via the conductive trace.

2. The body-mountable device of claim 1, wherein the elongate extension has a length between approximately 2 millimeters and approximately 6 millimeters.

3. The body-mountable device of claim 1, further comprising an antenna disposed on the flexible substrate, wherein the electronic components are configured to indicate data related to the detected property of the emitted light to an external device using the antenna.

4. The body-mountable device of claim 1, wherein the one or more electronic components include a memory configured to store the data related to the detected property of the emitted light.

5. The body-mountable device of claim 1, further comprising a light emitter, wherein the one or more electronic components are further configured to (iii) operate the light emitter to illuminate, via the optical fiber, the analyte-sensitive substance, and wherein the light emitted from the analyte-sensitive substance is emitted responsive to illumination by the light emitter.

6. The body-mountable device of claim 5, wherein the analyte-sensitive substance comprises a fluorophore, and wherein the detected property of the emitted light is a property of the fluorescence of the fluorophore.

7. The body-mountable device of claim 1, further comprising a further optical fiber disposed on the elongate extension of the flexible substrate, wherein the further optical fiber extends along a length of the elongate extension to the distal end of the elongate extension, and further comprising:

an optical substance, wherein the optical substance is disposed at the distal end of the elongate extension of the flexible substrate, and wherein the optical substance has an optical property that is less strongly affected by the analyte in the interstitial fluid than the optical property of the analyte-sensitive substance; and a further light detector, wherein the one or more electronic components are further configured to (iii) operate the further light detector to detect, via the further optical fiber, a property of light emitted from the optical substance.

8. The body-mountable device of claim 1, wherein the analyte-sensitive substance is disposed within a polymer, wherein the polymer is permeable to the analyte.

9. The body-mountable device of claim 8, wherein the polymer comprises 2-hydroxyethyl methacrylate units.

10. The body-mountable device of claim 1, wherein the analyte is glucose and wherein the analyte-sensitive substance comprises a boronic acid moiety.

11. The body-mountable device of claim 1, wherein the light detector is optically coupled to an end of the optical fiber.

12. A method comprising:
operating a body-mountable device, wherein the body-mountable device comprises:

a flexible substrate having a first side and a second side opposite the first side, wherein the flexible substrate is comprised by a single piece of material that is configured to be mounted to a skin surface and that is shaped to have an elongate extension having a distal end configured to extend beneath the skin surface to contact interstitial fluid;

an adhesive layer disposed on the first side of the flexible substrate, wherein the adhesive layer is configured to adhere the flexible substrate to the skin surface;

an optical fiber disposed on the elongate extension of the flexible substrate, wherein the optical fiber extends along a length of the elongate extension to the distal end of the elongate extension;

an analyte-sensitive substance, wherein the analyte-sensitive substance is disposed at the distal end of the elongate extension of the flexible substrate, and wherein the analyte-sensitive substance has an optical property affected by an analyte in the interstitial fluid;

a light detector;

one or more electronic components disposed on the single piece of material of the flexible substrate, wherein at least one of the one or more electronic components is disposed on the first side of the flexible substrate; and a conductive trace patterned on a surface of the flexible substrate, wherein at least one of the one or more electronic components is connected to the flexible substrate via the conductive trace; wherein the operating comprises:

obtaining, by the one or more electronic components operating the light detector to detect light emitted from the analyte-sensitive substance via the optical fiber, data related to a property of the emitted light; and indicating, by the one or more electronic components, the data related to the property of the emitted light.

13. The method of claim 12, wherein the body-mountable device further comprises a light emitter, and wherein the operating further comprises operating the light emitter to illuminate, via the optical fiber, the analyte-sensitive substance, and wherein the light received by the light detector from the analyte-sensitive substance is emitted from the analyte-sensitive substance responsive to illumination by the light emitter.

14. The method of claim 12, wherein the body-mountable device further comprises an antenna disposed on the flexible substrate, and wherein indicating, by the one or more electronic components, the data related to the property of the emitted light comprises:

communicating the data related to the property of the emitted light via the antenna to an external device.

15. The method of claim 12, wherein the one or more electronic components include a memory, wherein the operating further comprises:

storing the data related to the property of the emitted light in the memory.

16. The method of claim 12, further comprising:
coupling the elongate extension of the flexible substrate to a needle; and
inserting the needle with the elongate extension coupled thereto into the skin surface such that the analyte-sensitive substance is in a position to contact interstitial fluid.

17. The method of claim 16, further comprising:
retracting the needle from the skin surface such that the analyte-sensitive substance remains in the position to contact interstitial fluid.

18. The method of claim 12, wherein the body-mountable device further comprises: (a) a further optical fiber disposed on the elongate extension of the flexible substrate, wherein the further optical fiber extends along a length of the elongate extension to the distal end of the elongate extension, (b) an optical substance, wherein the optical substance is disposed at the distal end of the elongate extension, and wherein the optical substance has an optical property that is less strongly affected by the analyte in the interstitial fluid than the optical property of the analyte-sensitive substance, and (c) a further light detector, wherein the operating further comprises obtaining, by the one more electronic components operating the further light detector to receive further light from the optical substance via the further optical fiber, data related to a property of the received further light.

19. The method of claim 12, wherein the light detector is optically coupled to an end of the optical fiber.

* * * * *